(12) United States Patent
Charlson et al.

(10) Patent No.: US 10,360,996 B2
(45) Date of Patent: Jul. 23, 2019

(54) METHOD FOR SELECTIVELY ASSOCIATING CONTENT ITEMS WITH PRE-CONFIGURED ALTERNATIVES BASED UPON DIRECTED USER INPUT

(75) Inventors: Sara J. Charlson, Smithville, MO (US); Matthew R. Huffman, Lee's Summit, MO (US); Karen E. Berislavich, Liberty, MO (US); Jacqueline S. Lester, Kansas City, MO (US); Aaron L. Henton, Kansas City, MO (US); Jennifer L. Besch, Prairie Village, KS (US)

(73) Assignee: Cerner Innovation, Inc., Kansas City, KS (US)

( * ) Notice: Subject to any disclaimer, the term of this patent is extended or adjusted under 35 U.S.C. 154(b) by 1316 days.

(21) Appl. No.: 11/695,374

(22) Filed: Apr. 2, 2007

(65) Prior Publication Data
US 2007/0276869 A1 Nov. 29, 2007

Related U.S. Application Data

(60) Provisional application No. 60/788,559, filed on Mar. 31, 2006.

(51) Int. Cl.
*G16H 40/20* (2018.01)
*G16H 10/20* (2018.01)

(52) U.S. Cl.
CPC .................... *G16H 10/20* (2018.01)

(58) Field of Classification Search
CPC ........ G06Q 50/22; G06Q 10/10; G06Q 10/06; G06Q 50/24; G06Q 30/02; G06Q 30/04;
(Continued)

(56) References Cited

U.S. PATENT DOCUMENTS 5,325,293 A * 6/1994 Dorne ............................ 705/2
5,758,095 A * 5/1998 Albaum et al. .................. 705/2
(Continued)

OTHER PUBLICATIONS

Office Action dated Apr. 15, 2010 in U.S. Appl. No. 11/695,367.
(Continued)

*Primary Examiner* — John A Pauls
(74) *Attorney, Agent, or Firm* — Shook, Hardy & Bacon LLP

(57) ABSTRACT

Computerized methods for selectively associating content items with pre-configured alternatives based upon directed user input are provided. The method includes receiving a first content item; determining a plurality of pre-configured alternatives for association with the first content item, each of the plurality of pre-configured alternatives being determined utilizing one or more of pre-configured content, facility- and personnel-specific content, a facility and personnel profile, and informational assistance data; presenting the plurality of pre-configured alternatives for user selection; receiving user selection of one of the plurality of pre-configured alternatives for association with the first content item; receiving a second content item; and determining at least one pre-configured alternative for association with the second content item. The at least one-preconfigured alternative is a member of the plurality of pre-configured alternatives but is not the one of the plurality of pre-configured alternatives selected by the user for association with the first content item.

9 Claims, 27 Drawing Sheets

(58) Field of Classification Search
CPC ... G06Q 40/08; G06F 16/327; G06F 19/3418;
G06F 19/321; G06F 19/322; G06F
19/3425; G06F 19/3487; G06F 19/3456;
G16H 40/20
USPC .................... 704/9; 705/2–4; 707/1, 3, 102;
600/300; 719/316; 706/45
See application file for complete search history.

(56) References Cited

U.S. PATENT DOCUMENTS

| | | | |
|---|---|---|---|
| 6,047,259 A | | 4/2000 | Campbell et al. |
| 6,055,494 A * | | 4/2000 | Friedman ........................ 704/9 |
| 6,151,581 A | | 11/2000 | Kraftson et al. |
| 6,523,019 B1 * | | 2/2003 | Borthwick ...................... 706/45 |
| 6,678,669 B2 | | 1/2004 | Lapointe et al. |
| 6,687,685 B1 | | 2/2004 | Sadeghi et al. |
| 6,915,254 B1 * | | 7/2005 | Heinze et al. .................... 704/9 |
| 7,555,425 B2 * | | 6/2009 | Oon ................................ 704/9 |
| 7,610,192 B1 * | | 10/2009 | Jamieson ........................ 704/9 |
| 2001/0051879 A1 * | | 12/2001 | Johnson et al. ................. 705/2 |
| 2002/0035486 A1 | | 3/2002 | Huyn et al. |
| 2002/0120466 A1 * | | 8/2002 | Finn ................................ 705/2 |
| 2002/0128866 A1 * | | 9/2002 | Goetzke et al. ................. 705/2 |
| 2002/0165852 A1 * | | 11/2002 | Gogolak .......................... 707/3 |
| 2003/0036683 A1 * | | 2/2003 | Kehr et al. .................... 600/300 |
| 2003/0045958 A1 | | 3/2003 | Brandt et al. |
| 2003/0060688 A1 | | 3/2003 | Ciarniello et al. |
| 2003/0216937 A1 | | 11/2003 | Schreiber et al. |
| 2004/0019502 A1 * | | 1/2004 | Leaman et al. ................. 705/2 |
| 2004/0034610 A1 | | 2/2004 | De Lacharriere et al. |
| 2004/0044559 A1 | | 3/2004 | Malik et al. |
| 2004/0054685 A1 * | | 3/2004 | Rahn et al. .................. 707/102 |
| 2004/0078231 A1 * | | 4/2004 | Wilkes et al. ................... 705/2 |
| 2004/0078236 A1 * | | 4/2004 | Stoodley et al. ................ 705/2 |
| 2004/0220895 A1 * | | 11/2004 | Carus et al. ..................... 707/1 |
| 2004/0260666 A1 | | 12/2004 | Pestonik et al. |
| 2005/0138637 A1 * | | 6/2005 | Porter et al. .................. 719/316 |
| 2005/0182656 A1 * | | 8/2005 | Morey ............................. 705/2 |
| 2005/0182743 A1 | | 8/2005 | Koenig |
| 2006/0149416 A1 * | | 7/2006 | Mohapatra et al. .......... 700/242 |
| 2006/0168043 A1 * | | 7/2006 | Eisenberger et al. ......... 709/206 |
| 2007/0174090 A1 * | | 7/2007 | Friedlander et al. ............ 705/3 |
| 2008/0046292 A1 * | | 2/2008 | Myers et al. .................... 705/3 |

OTHER PUBLICATIONS

Office Action dated Apr. 12, 2010 in U.S. Appl. No. 11/695,362.
Non-Final Office Action dated Mar. 2, 2011 in U.S. Appl. No. 11/695,367.
Office Action dated Feb. 16, 2011 in U.S. Appl. No. 11/695,374.
Final Office Action dated Aug. 4, 2010 in U.S. Appl. No. 11/695,362.
Final Office Action dated Aug. 4, 2010 in U.S. Appl. No. 11/695,367.
Final Office Action dated Jun. 21, 2011 in U.S. Appl. No. 11/695,362.
Final Office Action dated Jul. 20, 2011 in U.S. Appl. No. 11/695,367.
Non-Final Office Action in U.S. Appl. No. 11/695,362, dated Dec. 16, 2013, 22 pages.
Non-Final Office Action in U.S. Appl. No. 11/695,367, dated Dec. 17, 2013, 23 pages.
Final Office Action dated Jul. 7, 2014 in U.S. Appl. No. 11/695,367, 18 pages.
Final Office Action dated Jul. 7, 2014 in U.S. Appl. No. 11/695,362, 14 pages.

* cited by examiner

☐ ORDER CATALOG DEFINITION

EXISTING ORDERABLE ITEMS

THE ORDERABLE ITEMS FROM YOUR EXISTING ORDER CATALOG ARE DISPLAYED BELOW.

CATALOG TYPE: LABORATORY   ACTIVITY TYPE: GENERAL LAB

AS YOU PROCEED THROUGH THIS WIZARD, THE SYSTEM WILL ATTEMPT TO RECONCILE THESE PREVIOUS ORDERABLE ITEMS WITH THE ORDERABLE ITEMS PROVIDED IN THE START DATABASE OF THE HEALTHCARE INFORMATION SYSTEM BEING IMPLEMENTED. IF THERE ARE ANY ITEMS IN THIS LIST THAT YOU WOULD LIKE TO EXCLUDE FROM CONSIDERATION, CLICK THE CORRESPONDING REMOVE CHECK BOXES. ONCE ITEMS ARE MATCHED, THEY WILL NO LONGER BE AVAILABLE FOR REMOVAL FROM THIS LIST. YOU CAN REVIEW THE COMPLETE LIST OF PREVIOUS ITEMS BY CLICKING "SHOW ALL PREVIOUS ORDERABLE ITEMS."

SHOW ALL ALL PREVIOUS ORDERABLE ITEMS.

PREVIOUS ORDERABLE ITEMS

| REMOVE | DISPLAY | DESCRIPTION |
|---|---|---|
| ☐ | 17 HYDROXY CORTICOSTEROIDS | 17 HYDROXY CORTICOSTEROIDS |
| ☐ | 17 KETOGENIC STEROIDS | 17 KETOGENIC STEROIDS |
| ☐ | 17 KETOSTEROIDS | 17 KETOSTEROIDS |
| ☐ | 5 HIAA URINE (SEROTONIN) | 5 HIAA URINE (SEROTONIN) |
| ☐ | 5 NUCLEOTIDASE | 5 NUCLEOTIDASE |
| ☐ | 68 KD HEAT SHOCK PROTEIN | 68 KD HEAT SHOCK PROTEIN |
| ☐ | 83520 ANTIHUM NEUT IGG CHRG ONLY | 83520 ANTIHUM NEUT IGG CHRG ONLY |
| ☐ | 83520 ANTIOMPC IGA CHRG ONLY | 83520 ANTIOMPC IGA CHRG ONLY |
| ☐ | 83520 SCEREVISIAE IGG CHRG ONLY | 83520 SCEREVISIAE IGG CHRG ONLY |
| ☐ | 83520 SCEREVISIAE IGA CHRG ONLY | 83520 SCEREVISIAE IGA CHRG ONLY |
| ▷ | AMYLASE SERUM | AMYLASE SERUM |
| ▷ | BASIC METABOLIC PROFILE | BASIC METABOLIC PROFILE |
| ▷ | BUN | BUN |
| ▷ | CALCIUM SERUM | CALCIUM SERUM |
| ▷ | CBS | CBS |
| ▷ | CPK SERUM | *CPK SERUM |
| ▷ | CREATININE SERUM | *CREATININE SERUM |
| ▷ | ELECTROLYTES SERUM | *ELECTROLYTES SERUM |
| ▷ | GLUCOSE ADDITIONAL CHG ONLY | *GLUCOSE ADDITIONAL CHG ONLY |
| ▷ | GLUCOSE SERUM | *GLUCOSE SERUM |
| ▷ | GLUCOSE TOLERANCE 3 HR | *GLUCOSE TOLERANCE 3 HR |
| ▷ | GLUCOSE TOLERANCE CHRG ONLY | *GLUCOSE TOLERANCE CHRG ONLY |
| ▷ | *HEMATOCRIT | *HEMATOCRIT |
| ▷ | *HEMATOCRIT CHG CHRG ONLY | *HEMATOCRIT CHG CHRG ONLY |
| ▷ | *HEMOGLOBIN | *HEMOGLOBIN |
| ▷ | *HEMOGLOBIN AND HEMATOCRIT | *HEMOGLOBIN AND HEMATOCRIT |

[ OK ]   [ CANCEL ]

FIG. 8.

☐ ORDER CATALOG DEFINITION

EXACT NAME MATCHES

THIS PAGE DISPLAYS EXACT NAME MATCHES BETWEEN YOUR PREVIOUS ORDERABLE ITEMS AND THE ORDERABLE ITEMS OF THE HEALTHCARE INFORMATION SYSTEM (HCIS) BEING IMPLEMENTED. AN EXACT MATCH OCCURS WHEN EITHER THE DISPLAY OR THE DESCRIPTION IS THE SAME AS THE PRIMARY NAME, LONG DESCRIPTION, DEPARTMENT NAME, DEPARTMENTAL SYNONYM OR CARE PROVIDER SYNONYM OF THE HEALTHCARE INFORMATION SYSTEM (HCIS) BEING IMPLEMENTED.

CATALOG TYPE: LABORATORY    ACTIVITY TYPE: GENERAL LAB

REVIEW THE EXACT MATCHES BELOW AND CLICK OK WHEN YOUR ARE FINISHED. TO EXCLUDE A MATCH, DESELECT THE CORRESPONDING MATCH CHECKBOX FOR THAT ORDERABLE ITEM.

EXACT NAME MATCHES (84)                                                                                  SHOW ALL ALL PREVIOUS ORDERABLE ITEMS.

| MATCH | DISPLAY | DESCRIPTION | HCIS NAME (PRIMARY SYNONYM) |
|---|---|---|---|
| ☑ | ACETONE QUANTITATIVE | ACETONE QUANTITATIVE | ACETONE QUANTITATIVE |
| ☑ | ACTH | ACTH | ACTH |
| ☑ | HEPATITIS PANEL ACUTE | HEPATITIS PANEL ACUTE | ACUTE HEPATITIS PANEL |
| ☑ | ALDOLASE | ALDOLASE | ALDOLASE |
| ☑ | ALDOSTERONE URINE | ALDOSTERONE URINE | ALDOSTERONE URINE |
| ☑ | AMMONIA | AMMONIA | AMMONIA LEVEL |
| ☑ | BETA 2 MICROGLOBULINE... | BETA 2 MICROGLOBULINE URINE | BETA 2 MICROGLOBULINE URINE |
| ☑ | BILIRUBIN TOTAL | BILIRUBIN TOTAL | BILIRUBIN TOTAL |
| ☑ | BLEEDING TIME | BLEEDING TIME | BLEEDING TIME |
| ☑ | BUN | BUN | BUN |
| ☑ | CRP HIGH SENSITIVITY | CRP HIGH SENSITIVITY | C-REACTIVE PROTEIN HIGH SENSITIVITY |
| ☑ | C1 ESTERASE INHIBITOR | C1 ESTERASE INHIBITOR | C1 ESTERASE INHIBITOR |
| ☑ | CALCITONIN | CALCITONIN | CALCITONIN LEVEL |
| ☑ | CARDIOLIPIN ANTIBODY... | CARDIOLIPIN ANTIBODY IGA | CARDIOLIPIN ANTIBODY IgA |
| ☑ | CAROTENE | CAROTENE | CAROTENE |
| ☑ | CSF CELL COUNT | CSF CELL COUNT | CELL COUNT W/ DIFF CSF |
| ☑ | CERULOPLASMIN | CERULOPLASMIN | CERULOPLASMIN |
| ☑ | HDL | HDL | CHOLESTEROL HDL |
| ☑ | CHOLESTEROL TOTAL | CHOLESTEROL TOTAL | CHOLESTEROL TOTAL |
| ☑ | CHROMOGRANIN A | CHROMOGRANIN A | CHROMOGRANIN A |
| ☑ | CHROMOSOME ANALYSIS | CHROMOSOME ANALYSIS | CHROMOSOME ANALYSIS |
| ☑ | CYTOMEGALOVIRUS ANT... | CYTOMEGALOVIRUS ANTIBODY IGG | CYTOMEGALOVIRUS ANTIBODY IgG |
| ☑ | CRYOGLOBULIN | CRYOGLOBULIN | CRYOGLOBULIN |
| ☑ | CRYPTOCOCCAL ANTIGE... | CRYPTOCOCCAL ANTIGEN CSF | CRYPTOCOCCAL ANTIGEN CSF |
| ☑ | ENTEROVIRUS BY PCR | ENTEROVIRUS BY PCR | ENTEROVIRUS BY PCR |
| ☑ | ESTRIOL | ESTRIOL | ESTRIOL LEVEL |
| ☑ | ETHYLENE GLYCOL | ETHYLENE GLYCOL | ETHYLENE GLYCOL LEVEL |
| ☑ | FACTOR XI | FACTOR XI | FACTOR XI ASSAY |

[ OK ]   [ CANCEL ]

FIG. 10.

☐ ORDER CATALOG DEFINITION

ONE-TO-ONE MATCHES

THIS PAGE DISPLAYS ONE-TO-ONE MATCHES THAT OCCUR BETWEEN ONE PREVIOUS ORDERABLE ITEM AND ONE ORDERABLE ITEM OF THE HEALTHCARE INFORMATION SYSTEM BEING IMPLEMENTED BASED ON A DATABASE CONSISTING OF OTHER COMMON ORDER NAMES AND CPT CODES.

CATALOG TYPE: LABORATORY    ACTIVITY TYPE: GENERAL LAB

REVIEW THE ONE-TO-ONE MATCHES BELOW AND CLICK OK WHEN YOUR ARE FINISHED. THE MATCH TYPE AND MATCH VALUE COLUMNS SHOW THE PARAMETER ON WHICH THE MATCH OCCURRED, ALONG WITH MATCHING VALUE. TO EXCLUDE A MATCH, DESELECT THE CORRESPONDING MATCH CHECKBOX FOR THAT ORDERABLE ITEM.

☐ SHOW ALL ALL PREVIOUS ORDERABLE ITEMS.

ONE-TO-ONE MATCHES (185)

| MATCH | DISPLAY | DESCRIPTION | MILLENNIUM NAME (PRIMARY SYNONYM) | MATCH TYPE | MATCH VALUE |
|---|---|---|---|---|---|
| ☑ | 17-HYDROXY CORTICOSTEROIDS | 17-HYDROXY CORTICOSTEROIDS | 17-HYDROXYCORTICOSTEROIDS 24 HOUR URINE | CPT4 | 83491 |
| ☑ | 17 KETOGENIC STEROIDS | 17 KETOGENIC STEROIDS | 17 KETOGENIC STEROIDS 24 HOUR URINE | CPT4 | 83582 |
| ☑ | 17 KETOSTEROIDS | 17 KETOSTEROIDS | 17 KETOSTEROIDS TOTAL 24 HOUR URINE | CPT4 | 83586 |
| ☑ | 5 HIAA URINE (SEROTONIN) | 5 HIAA URINE (SEROTONIN) | 5 HIAA 24 HOUR URINE | CPT4 | 83497 |
| ☑ | 5 NUCLEOTIDASE | 5 NUCLEOTIDASE | 5 NUCLEOTIDASE | CPT4 | 83915 |
| ☑ | ACETAMINOPHEN | ACETAMINOPHEN | ACETAMINOPHEN LEVEL | ALTERNATE NAME | ACETAMINOPHEN |
| ☑ | CHOLINESTERASE RBC CHRG ONLY | CHOLINESTERASE RBC CHRG ONLY | ACETYLCHOLINESTERASE RED BLOOD CELL | CPT4 | 82482 |
| ☑ | ACID PHOSPHATASE TOTAL | ACID PHOSPHATASE TOTAL | ACID PHOSPHATASE | CPT4 | 84060 |
| ☑ | ALBUMIN SERUM | ALBUMIN SERUM | ALBUMIN LEVEL | ALTERNATE NAME | ALBUMIN SERUM |
| ☑ | ALDOSTERONE SERUM | ALDOSTERONE SERUM | ALDOSTERONE | CPT4 | 82088 |
| ☑ | ALPHA 1 ANTITRYPSIN | ALPHA 1 ANTITRYPSIN | ALPHA 1-ANTITRYPSIN | ALTERNATE NAME | ALPHA 1 ANTITRYPSIN |
| ☑ | ALT (SGPT) | ALT (SGPT) | ALT | ALTERNATE NAME | ALT (SGPT) |
| ☑ | AMIKACIN PEAK | AMIKACIN PEAK | AMIKACIN LEVEL PEAK | ALTERNATE NAME | AMIKACIN PEAK |
| ☑ | AMIKACIN TROUGH | AMIKACIN TROUGH | AMIKACIN LEVEL TROUGH | ALTERNATE NAME | AMIKACIN TROUGH |
| ☑ | URINE CYSTINE QUANTITATIVE SINGLE | URINE CYSTINE QUANTITATIVE SINGLE | AMINO ACID QUANTITATIVE | CPT4 | 82131 |
| ☑ | AMIODARONE | AMIODARONE | AMIODARONE LEVEL | ALTERNATE NAME | AMIODARONE |
| ☑ | AMITRY.NORTRYP I CHRG ONLY | AMITRY.NORTRYP I CHRG ONLY | AMITRIPTYLINE LEVEL | CPT4 | 80152 |
| ☑ | AMYLASE SERUM | AMYLASE SERUM | AMYLASE LEVEL | ALTERNATE NAME | AMYLASE SERUM |
| ☑ | ANGIOTENSIN CONVERT ENZYME | ANGIOTENSIN CONVERT ENZYME | ANGIOTENSIN CONVERTING ENZYME | ALTERNATE NAME | ANGIOTENSIN CONVERT ENZYME |
| ☑ | ANTI DNASE STREPTOCOCCAL | ANTI DNASE STREPTOCOCCAL | ANTIDNASE B TITER | CPT4 | 86215 |
| ☑ | AST (SGOT) | AST (SGOT) | AST | AST | AST (SGOT) |
| ☑ | BASIC METABOLIC PROFILE 2000 | BASIC METABOLIC PROFILE 2000 | BASIC METABOLIC PANEL | CPT4 | 80048 |
| ☑ | BETA 2 MICROGLOBULIN SERUM | BETA 2 MICROGLOBULIN SERUM | BETA 2 MICROGLOBULIN | CPT4 | 82232 |
| ☑ | PREGNANCY TEST SERUM | PREGNANCY TEST SERUM | BETA hCG QUALITATIVE | ALTERNATE NAME | PREGNANCY TEST SERUM |
| ☑ | PREGNANCY TEST URINE | PREGNANCY TEST URINE | BETA hCG QUALITATIVE URINE | ALTERNATE NAME | PREGNANCY TEST URINE |
| ☑ | HCG QUANT | HCG QUANT | BETA hCG QUANTITATIVE | ALTERNATE NAME | HCGQUANT |

[ OK ]   [ CANCEL ]

☐ ORDER CATALOG DEFINITION

ONE-TO-MANY MATCHES

THIS PAGE DISPLAYS ONE-TO-MANY MATCHES THAT HAVE OCCURRED BETWEEN ONE PREVIOUS ORDERABLE ITEM AND MULTIPLE ORDERABLE ITEMS OF THE HEALTHCARE INFORMATION SYSTEM BEING IMPLEMENTED BASED ON CPT CODES.

CATALOG TYPE: LABORATORY    ACTIVITY TYPE: GENERAL LAB

TO SELECT THE ORDERABLE ITEM THAT MATCHES A CORRESPONDING PREVIOUS ORDERABLE ITEM, CLICK THE MULTIPLE MATCHES LINK TO DISPLAY THE OPTIONS. CLICK OK WHEN YOU HAVE COMPLETED ALL THE MATCHES. THE MATCH TYPE AND MATCH VALUE COLUMNS SHOW THE PARAMETER ON WHICH THE MATCH OCCURRED, ALONG WITH MATCHING VALUE. TO CANCEL OR EXCLUDE A MATCH, DESELECT THE CORRESPONDING MATCH CHECKBOX OR THAT ORDERABLE ITEM.

SHOW ALL ALL PREVIOUS ORDERABLE ITEMS.

ONE-TO-MANY MATCHES (185)

| MATCH | DISPLAY | DESCRIPTION | HCIS NAME (PRIMARY SYNONYM) | MATCH TYPE | MATCH VALUE |
|---|---|---|---|---|---|
| ☐ | 83520 ANTIHUM NEU... | 83520 ANTIHUM NEUTIGG CHRG ONLY | MULTIPLE MATCHES | | |
| ☐ | 83520 ANTIOMPC IG... | 83520 ANTIOMPC IGA CHRG ONLY | MULTIPLE MATCHES | | |
| ☐ | 83520 SCEREVISIAE... | 83520 SCEREVISIAE IGG CHRG ONLY | MULTIPLE MATCHES | | |
| ☐ | 83520 SCERVISIAE I... | 83520 SCERVISIAE IGA CHRG ONLY | MULTIPLE MATCHES | | |
| ☐ | NEONATAL BILIRUBIN | NEONATAL BILIRUBIN | MULTIPLE MATCHES | | |
| ☐ | ONE HOUR POST G... | ONE HOUR POST GLUCOLA GLUCOSE | MULTIPLE MATCHES | | |
| ☐ | POTASSIUM SERUM | POTASSIUM SERUM | MULTIPLE MATCHES | | |
| ☐ | URINALYSIS | URINALYSIS | MULTIPLE MATCHES | | |
| ☐ | WBC | WBC | MULTIPLE MATCHES | | |
| ☐ | ACETONE/KETONE U... | ACETONE/KETONE URINE QUALITATIVE | MULTIPLE MATCHES | | |
| ☑ | ACETYLCHOLINE BIN... | ACETYLCHOLINE BINDING ANTIBODY | ACETYLCHOLINE RECEPTOR BINDING A... | CPT4 | 84238 |
| ☐ | ACETYLCHOLINE BLO... | ACETYLCHOLINE BLOCKING ANTIBODY | MULTIPLE MATCHES | | |
| ☐ | ACHR BINDING AB C... | ACHR BINDING AB CHRG ONLY | MULTIPLE MATCHES | | |
| ☐ | ACHR BLOCKING AB... | ACHR BLOCKING AB CHRG ONLY | MULTIPLE MATCHES | | |
| ☐ | ACHR MODULATING... | ACHR MODULATING AB CHRG ONLY | MULTIPLE MATCHES | | |
| ☐ | AFP MULTISCREEN A... | AFP MULTISCREEN AFP CHG CHG ONLY | MULTIPLE MATCHES | | |
| ☐ | AFP QUAD 82105 CH... | AFP QUAD 82105 CHRG ONLY | MULTIPLE MATCHES | | |
| ☐ | AFP TUMOR MARKER | AFP TUMOR MARKER | MULTIPLE MATCHES | | |
| ☐ | ALCOHOL (ETHANOL) | ALCOHOL (ETHANOL) | MULTIPLE MATCHES | | |
| ☐ | ALPHA FETOPROTEI... | ALPHA FETOPROTEIN (NTD) | MULTIPLE MATCHES | | |
| ☐ | AMINO ACID SCREEN... | AMINO ACID SCREEN URINE MULTI | MULTIPLE MATCHES | | |
| ☐ | AMINO ACIDS SCREE... | AMINO ACIDS SCREEN PLASMA MULTI | MULTIPLE MATCHES | | |
| ☐ | AMYLASE MISC FLUID | AMYLASE MISC FLUID | MULTIPLE MATCHES | | |
| ☐ | AMYLASE URINE RAN... | AMYLASE URINE RANDOM | MULTIPLE MATCHES | | |
| ☐ | ANA PROFILE 83520 | ANA PROFILE 83520 CHRG ONLY | MULTIPLE MATCHES | | |
| ☐ | ANA PROFILE 86160 | ANA PROFILE 86160 1ST CHRG ONLY | MULTIPLE MATCHES | | |

[ OK ]    [ CANCEL ]

FIG. 17.

☐ ORDER CATALOG DEFINITION

ONE-TO-MANY MATCHES

THIS PAGE DISPLAYS ONE-TO-MANY MATCHES THAT HAVE OCCURRED BETWEEN ONE PREVIOUS ORDERABLE ITEM AND MULTIPLE ORDERABLE ITEMS OF THE HEALTHCARE INFORMATION SYSTEM BEING IMPLEMENTED BASED ON CPT CODES.

CATALOG TYPE: LABORATORY    ACTIVITY TYPE: GENERAL LAB

TO SELECT THE ORDERABLE ITEM THAT MATCHES A CORRESPONDING PREVIOUS ORDERABLE ITEM, CLICK THE MULTIPLE MATCHES LINK TO DISPLAY THE OPTIONS. CLICK OK WHEN YOU HAVE COMPLETED ALL THE MATCHES. THE MATCH TYPE AND MATCH VALUE COLUMNS SHOW THE PARAMETER ON WHICH THE MAT...
CORRESPONDING MATCH CHECK  ☐ ACETYLCHOLINE BLOCKING ANTIBODY — 1800

THIS PAGE DISPLAYS THE MATCHES THAT HAVE OCCURRED BETWEEN ONE PREVIOUS ORDERABLE ITEM AND MULTIPLE ORDERABLE ITEMS OF THE HEALTHCARE INFORMATION SYSTEM BEING IMPLEMENTED BASED ON CPT CODE.

SOME MULTIPLE MATCHES YOU HAVE ASSIGNED TO OTHER ORDERABLES AND HAVE BEEN REMOVED FROM THIS LIST. ─1810

| HCIS NAME (PRIMARY SYNONYM) | MATCH TYPE | MATCH VALUE |
|---|---|---|
| ACETYLCHOLINE RECEPTOR BLOCKING ANTIBODY | CPT4 | 84238 |

1812 — [ OK ]  [ CANCEL ]

ONE-TO-MANY MATCHES (185)

| MATCH | DISPLAY | DESC | | |
|---|---|---|---|---|
| ☐ | 83520 ANTIHUM NEU... | 83520 | | |
| ☐ | 83520 ANTIOMPC TG... | 83520 | | |
| ☐ | 83520 SCEREVISIAE... | 83520 | | |
| ☐ | 83520 SCERVISIAE I... | 83520 | | |
| ☐ | NEONATAL BILIRUBIN | NEON | | |
| ☐ | ONE HOUR POST GL... | ONE | | |
| ☐ | POTASSIUM SERUM | POTA | | |
| ☐ | URINALYSIS | URIN | | |
| ☐ | WBC | WBC | | |
| ☐ | ACETONE/KETONE U... | ACET | | |
| ☑ | ACETYLCHOLINE BIN... | ACET | | |
| ☐ | ACETYLCHOLINE BLO... | ACET | | |
| ☐ | ACHR BINDING AB C... | ACHR | | |
| ☐ | ACHR BLOCKING AB ... | ACHR | | |
| ☐ | ACHR MODULATING ... | ACHR | | |
| ☐ | AFP MULTISCREEN A... | AFP MULTISCREEN APP CHG CHG ONLY | MULTIPLE MATCHES | |
| ☐ | AFP QUAD 82105 CH... | AFP QUAD 82105 CHRG ONLY | MULTIPLE MATCHES | |
| ☐ | AFP TUMOR MARKER | AFP TUMOR MARKER | MULTIPLE MATCHES | |
| ☐ | ALCOHOL (ETHANOL) | ALCOHOL (ETHANOL) | MULTIPLE MATCHES | |
| ☐ | ALPHA FETOPROTEI... | ALPHA FETOPROTEIN (NTD) | MULTIPLE MATCHES | |
| ☐ | AMINO ACID SCREEN... | AMINO ACID SCREEN URINE MULTI | MULTIPLE MATCHES | |
| ☐ | AMINO ACIDS SCREE... | AMINO ACIDS SCREEN PLASMA MULTI | MULTIPLE MATCHES | |
| ☐ | AMYLASE MISC FLUID | AMYLASE MISC FLUID | MULTIPLE MATCHES | |
| ☐ | AMYLASE URINE RAN... | AMYLASE URINE RANDOM | MULTIPLE MATCHES | |
| ☐ | ANA PROFILE 83520 | ANA PROFILE 83520 CHRG ONLY | MULTIPLE MATCHES | |
| ☐ | ANA PROFILE 86160 | ANA PROFILE 86160 1ST CHRG ONLY | MULTIPLE MATCHES | |

[ OK ]  [ CANCEL ]

FIG. 18.

ORDER CATALOG DEFINITION

ONE-TO-MANY MATCHES

THIS PAGE DISPLAYS ONE-TO-MANY MATCHES THAT HAVE OCCURRED BETWEEN ONE PREVIOUS ORDERABLE ITEM AND MULTIPLE ORDERABLE ITEMS OF THE HEALTHCARE INFORMATION SYSTEM BEING IMPLEMENTED BASED ON CPT CODES.

CATALOG TYPE: LABORATORY    ACTIVITY TYPE: GENERAL LAB

TO SELECT THE ORDERABLE ITEM THAT MATCHES A CORRESPONDING PREVIOUS ORDERABLE ITEM, CLICK THE MULTIPLE MATCHES LINK TO DISPLAY THE OPTIONS. CLICK OK WHEN YOU HAVE COMPLETED ALL THE MATCHES. THE MATCH TYPE AND MATCH VALUE COLUMNS SHOW THE PARAMETER ON WHICH THE MATCH OCCURRED, ALONG WITH MATCHING VALUE. TO CANCEL OR EXCLUDE A MATCH, DESELECT THE CORRESPONDING MATCH CHECKBOX OR THAT ORDERABLE ITEM.

SHOW ALL ALL PREVIOUS ORDERABLE ITEMS.

ONE-TO-MANY MATCHES (185)

| MATCH | DISPLAY | DESCRIPTION | HCIS NAME (PRIMARY SYNONYM) | MATCH TYPE | MATCH VALUE |
|---|---|---|---|---|---|
| ☐ | 83520 ANTIHUM NEU... | 83520 ANTIHUM NEUT/IGG CHRG ONLY | MULTIPLE MATCHES | | |
| ☐ | 83520 ANTIOMPC IG... | 83520 ANTIOMPC IGA CHRG ONLY | MULTIPLE MATCHES | | |
| ☐ | 83520 SCEREVISIAE... | 83520 SCEREVISIAE IGG CHRG ONLY | MULTIPLE MATCHES | | |
| ☐ | 83520 SCEREVISIAE I... | 83520 SCEREVISIAE IGA CHRG ONLY | MULTIPLE MATCHES | | |
| ☐ | NEONATAL BILIRUBIN | NEONATAL BILIRUBIN | MULTIPLE MATCHES | | |
| ☐ | ONE HOUR POST GL... | ONE HOUR POST GLUCOLA GLUCOSE | MULTIPLE MATCHES | | |
| ☐ | POTASSIUM SERUM | POTASSIUM SERUM | MULTIPLE MATCHES | | |
| ☐ | URINALYSIS | URINALYSIS | MULTIPLE MATCHES | | |
| ☐ | WBC | WBC | MULTIPLE MATCHES | | |
| ☐ | ACETONE/KETONE U... | ACETONE/KETONE URINE QUALITATIVE | MULTIPLE MATCHES | | |
| ☑ | ACETYLCHOLINE BIN... | ACETYLCHOLINE BINDING ANTIBODY | ACETYLCHOLINE RECEPTOR BINDING A... | CPT 4 | 84238 |
| ☐ | ACETYLCHOLINE BLO... | ACETYLCHOLINE BLOCKING ANTIBODY | ACETYLCHOLINE RECEPTOR BLOCKING... | CPT 4 | 84238 |
| ☐ | ACHR BINDING AB C... | ACHR BINDING AB CHRG ONLY | MULTIPLE MATCHES | | |
| ☐ | ACHR BLOCKING AB... | ACHR BLOCKING AB CHRG ONLY | MULTIPLE MATCHES | | |
| ☐ | ACHR MODULATING... | ACHR MODULATING AB CHRG ONLY | MULTIPLE MATCHES | | |
| ☐ | AFP MULTISCREEN A... | AFP MULTISCREEN AFP CHG CHG ONLY | MULTIPLE MATCHES | | |
| ☐ | AFP QUAD 82105 CH... | AFP QUAD 82105 CHRG ONLY | MULTIPLE MATCHES | | |
| ☐ | AFP TUMOR MARKER | AFP TUMOR MARKER | MULTIPLE MATCHES | | |
| ☐ | ALCOHOL (ETHANOL) | ALCOHOL (ETHANOL) | MULTIPLE MATCHES | | |
| ☐ | ALPHA FETOPROTEI... | ALPHA FETOPROTEIN (NTD) | MULTIPLE MATCHES | | |
| ☐ | AMINO ACID SCREEN... | AMINO ACID SCREEN URINE MULTI | MULTIPLE MATCHES | | |
| ☐ | AMINO ACIDS SCREE... | AMINO ACIDS SCREEN PLASMA MULTI | MULTIPLE MATCHES | | |
| ☐ | AMYLASE MISC FLUID | AMYLASE MISC FLUID | MULTIPLE MATCHES | | |
| ☐ | AMYLASE URINE RAN... | AMYLASE URINE RANDOM | MULTIPLE MATCHES | | |
| ☐ | ANA PROFILE 83520 | ANA PROFILE 83520 CHRG ONLY | MULTIPLE MATCHES | | |
| ☐ | ANA PROFILE 86160 | ANA PROFILE 86160 1ST CHRG ONLY | MULTIPLE MATCHES | | |

[ OK ]   [ CANCEL ]

FIG. 19.

☐ ORDER CATALOG DEFINITION

PERFORM MANUAL MATCHING

THIS PAGE DISPLAYS THE REMAINING PREVIOUS ORDERABLE ITEMS THAT WERE NOT AUTOMATICALLY MATCHED IN A PREVIOUS STEP.

| CATALOG TYPE: LABORATORY | ACTIVITY TYPE: GENERAL LAB |
|---|---|

TO MANUALLY CREATE A MATCH, SELECT AN UNMATCHED PREVIOUS ORDERABLE ITEM FROM THE PREVIOUS ORDERABLE ITEMS LIST. IF PROPOSED ORDERABLE ITEMS FOR THAT PREVIOUS ITEM EXISTS THEY ARE DISPLAYED IN THE ORDERABLE ITEMS LIST, SELECT THE ORDERABLE ITEMS THAT MATCHES THE PREVIOUS ITEM AND CLICK MATCH (OR DOUBLE-CLICK THE ITEM). IF NO PROPOSED ITEMS EXIST FOR THAT ITEM, OR IF THE ITEMS IN THE IN THE PROPOSED LIST ARE NOT ACCURATE, CLICK THE ALL TAB TO VIEW A LIST OF ALL ORDERABLE ITEMS OF THE HEALTHCARE INFORMATION SYSTEM (HCIS) BEING IMPLEMENTED THAT ARE AVAILABLE TO MATCH.

PREVIOUS ORDERABLE ITEMS

| DISPLAY | DESCRIPTION |
|---|---|
| AFP QUAD 82105 CHRG ONLY | AFP QUAD 82105 CHRG ONLY |
| AFP QUAD 82677 CHRG ONLY | AFP QUAD 82677 CHRG ONLY |
| AFP QUAD 84702 CHRG ONLY | AFP QUAD 84702 CHRG ONLY |
| AFP TUMOR MARKER | AFP TUMOR MARKER |
| ALKALINE PHOSPHATASE B... | ALKALINE PHOSPHATASE BONE SPECIFI |
| ALPHA FETOPROTEIN (NTD) | ALPHA FETOPROTEIN (NTD) |

● STARTS WITH  ○ CONTAINS   [   ] [FIND NEXT]

[ MATCH ]

PROPOSED | ALL

| HCIS NAME (PRIMARY SYNONYM) | MATCH |
|---|---|
| AFP MATERNAL | 79% |
| AFP AMNIOTIC FLUID | 79% |
| ALPHAN FETOPROTEIN TUMOR MARKER | 75% |
| RIBONUCLEOPROTEIN ANTIBODY | 35% |
| APOLIPOPROTEIN A | 34% |

● STARTS WITH  ○ CONTAINS   [   ] [FIND NEXT]

REVIEW THE MANUAL MATCHES YOU HAVE CREATED AND CLICK OK WHEN YOU ARE READY TO PROCEED.

MANUALLY-DEFINED MATCHES

| DISPLAY | DESCRIPTION | MILLENNIUM NAME (PRIMARY SYNONYM) |
|---|---|---|
| ALCOHOL (ETHANOL) | ALCOHOL (ETHANOL) | ETHANOL LEVEL |
| ALKALINE PHOSPHATASE SERUM | ALKALINE PHOSPHATASE SERUM | ALKALINE PHOSPHATASE |
| | | |
| | | |
| | | |
| | | |

[ REMOVE ]   [ REVIEW ALL PREVIOUS MATCHES ]

2100

2110 → [ OK ]   [ CANCEL ]

FIG. 21.

| ☐ ORDER CATALOG DEFINITION | | | | |
|---|---|---|---|---|
| PREVIOUS UNMATCHED ORDERABLES | | | | |
| THE PREVIOUS ORDERABLE ITEMS FOR WHICH NO EQUIVALENT WAS FOUND IN THE HEALTHCARE INFORMATION SYSTEM BEING IMPLEMENTED ARE DISPLAYED BELOW. | | | | |
| CATALOG TYPE: LABORATORY    ACTIVITY TYPE: GENERAL LAB | | | | |
| REVIEW THE UNMATCHED PREVIOUS ORDERABLE ITEMS AND CLICK THE CORRESPONDING ADD CHECK BOX FROM EACH ITEM YOU WANT TO ADD TO YOUR ORDER CATALOG. TO ADD ALL ITEMS TO YOUR ORDER CATALOG, CLICK SELECT ALL. AFTER YOU SELECT AN ITEM TO BE ADDED, YOU CAN CLICK THE PROPOSED NAME BOX TO CHANGE THE PROPOSED NAME, AND YOU CAN ADD A SUBACTIVITY TYPE BY SELECTING IT FROM THE CORRESPONDING SUBACTIVITY TYPE DROP-DOWN LIST. | | | | |
| NOT MATCHED ORDERABLES | | | | |
| ADD | DISPLAY | DESCRIPTION | NAME (PRIMARY SYNONYM) | SUBACTIVITY TYPE |
| ☐ | URINALYSIS | URINALYSIS | URINALYSIS | |
| ☐ | WBC | WBC | WBC | |
| ☐ | ACETONE/KETO... | ACETONE/KETONE URINE QUALITATIVE | ACETONE/KETONE URINE QUALITATIVE | |
| ☐ | ACETYLCHOLIN... | ACETYLCHOLINE RECEPTOR AB PANEL | ACETYLCHOLINE RECEPTOR AB PANEL | |
| ☐ | ACHR BINDING... | ACHR BINDING AB CHARG ONLY | ACHR BINDING AB CHARG ONLY | |
| ☐ | ACHR BLOCKIN... | ACHR BLOCKING AB CHARG ONLY | ACHR BLOCKING AB CHARG ONLY | |
| ☐ | ACHR MODULAT... | ACHR MODULATING AB CHRG ONLY | ACHR MODULATING AB CHRG ONLY | |
| ☐ | ACTINOMYCES... | ACTINOMYCES CULTURE | ACTINOMYCES CULTURE | |
| ☐ | ADENOVIRUS D... | ADENOVIRUS DIRECT ANTIGEN | ADENOVIRUS DIRECT ANTIGEN | |
| ☐ | AFP ALPHA FET... | AFP ALPHA FETO PROTEIN | AFP ALPHA FETO PROTEIN | |
| ☐ | AFP MULTISCREEN | AFP MULTISCREEN | AFP MULTISCREEN PANEL | CHEMISTRY |
| ☐ | AFP MULTISCRE... | AFP MULTISCREEN AFP CHG CHG ONLY | AFP MULTISCREEN AFP CHG CHG ONLY | |
| ☐ | AFP MULTISCRE... | AFP MULTISCREEN ESTRIOL CHG ONLY | AFP MULTISCREEN ESTRIOL CHG ONLY | |
| ☐ | AFP MULTISCRE... | AFP MULTISCREEN HCG QT CHG | AFP MULTISCREEN HCG QT CHG | |
| ☐ | AFP QUAD 8210... | AFP QUAD 82105 CHRG ONLY | AFP QUAD 82105 CHRG ONLY | |
| ☐ | AFP QUAD 8267... | AFP QUAD 82677 CHRG ONLY | AFP QUAD 82677 CHRG ONLY | |
| ☐ | AFP QUAD 8470... | AFP QUAD 84702 CHRG ONLY | AFP QUAD 84702 CHRG ONLY | |
| ☐ | AFP TUMOR MA... | AFP TUMOR MARKER | AFP TUMOR MARKER | |
| ☐ | ALKALINE PHOS... | ALKALINE PHOSPHATASE BONE SPECIFI | ALKALINE PHOSPHATASE BONE SPECIFI | |
| ☐ | ALPHA FETOPR... | ALPHA FETOPROTEIN (NTD) | ALPHA FETOPROTEIN (NTD) | |

⦿ STARTS WITH  ◯ CONTAINS  [____] [FIND NEXT]

[SELECT ALL]

[OK]  [CANCEL]  ⟵ 2310

☐ ORDER CATALOG DEFINITION

SELECT UNMATCHED ORDERABLE ITEMS

THE ORDERABLE ITEMS OF THE HEALTHCARE INFORMATION SYSTEM BEING IMPLEMENTED THAT HAVE NOT BEEN MATCHED ARE DISPLAYED BELOW.

CATALOG TYPE: LABORATORY  ACTIVITY TYPE: GENERAL LAB

REVIEW THE ORDERABLE ITEMS. COMMONLY PERFORMED ITEMS ARE PRESENTED AT THE TOP OF THE LIST AND ARE PRE-SELECTED. IF YOU DO NOT WANT TO ADD ONE OR MORE OF THESE ITEMS TO YOUR ORDER CATALOG, DESELECT THE CORRESPONDING CHECK BOXES. ADDITIONAL ORDER CATALOG OPTIONS ARE AVAILABLE BELOW THE COMMONLY-PERFORMED ITEMS. CLICK THE CORRESPONDING ADD CHECK BOX FOR EACH ITEM YOU WANT TO ADD TO YOUR ORDER CATALOG. TO ADD ALL ITEMS TO YOUR ORDER CATALOG, CLICK SELECT ALL.

NOT MATCHED ORDERABLES

| ADD | DISPLAY | DESCRIPTION |
|---|---|---|
| ☐ | 11-DEOXYCORTISOL | 11-DEOXYCORTISOL |
| ☐ | 17-HYDROXYPROGESTERONE URINE | 17-HYDROXYPROGESTERONE URINE |
| ☐ | 17-HYDROXYPROGESTERONE | 17-HYDROXYPROGESTERONE |
| ☐ | 17-d HYDROXYPROGESTERONE AMNIOTIC FLUID | 17-d HYDROXYPROGESTERONE AMNIOTIC FLUID |
| ☐ | 17-HYDROXYPROGESTERONE | 17-HYDROXYPROGESTERONE |
| ☐ | 18-HYDROXYPROGESTERONE | 18-HYDROXYPROGESTERONE |
| ☐ | ABSOLUTE LYMPHOCYTE COUNT | ABSOLUTE LYMPHOCYTE COUNT |
| ☐ | ABSOLUTE NEUTROPHIL COUNT | ABSOLUTE NEUTROPHIL COUNT |
| ☐ | ACETONE | ACETONE |
| ☐ | ACETYLCHOLINE RECEPTOR MODULATING ANTIBODY | ACETYLCHOLINE RECEPTOR MODULATING ANTIBODY |
| ☐ | ACETYLCHOLINESTERASE AMNIOTIC FLUID | ACETYLCHOLINESTERASE AMNIOTIC FLUID |
| ☐ | ACID PHOSPHATASE STAIN | ACID PHOSPHATASE STAIN |
| ☐ | ACYCLOVIR LEVEL | ACYCLOVIR LEVEL |
| ☐ | ACYLCARNITINES QUALITATIVE | ACYLCARNITINES QUALITATIVE |
| ☐ | ACYLCARNITINES QUANTITATIVE | ACYLCARNITINES QUANTITATIVE |
| ☐ | ADENOVIRUS ANTIBODY IgG | ADENOVIRUS ANTIBODY IgG |
| ☐ | ADENOVIRUS ANTIBODY IgG AND IgM | ADENOVIRUS ANTIBODY IgG AND IgM |
| ☐ | ADENOVIRUS ANTIBODY IgM | ADENOVIRUS ANTIBODY IgM |
| ☐ | ADENOVIRUS ANTIBODY TITER | ADENOVIRUS ANTIBODY TITER |
| ☐ | ADH LEVEL | ANTIDIURETIC HORMONE LEVEL |

⦿ STARTS WITH  ○ CONTAINS  [         ] [FIND NEXT]

[SELECT ALL]                                           [OK]   [CANCEL]

FIG. 25.

☐ ORDER CATALOG DEFINITION

ADD ORDERABLE ITEMS
USE THIS PAGE TO ADD NEW ORDERABLES TO YOUR ORDER CATALOG.

CATALOG TYPE: LABORATORY    ACTIVITY TYPE: GENERAL LAB

TO ADD A NEW ORDERABLE ITEM, ENTER THE NAME AND CLICK ADD ORDERABLE.

```
┌─ NEW ORDERABLE ─────────────────────────────────┐
│  LONG DESCRIPTION:*                             │
│  NAME:*                                         │
│  DEPARTMENT NAME:*                              │
│  CATALOG TYPE:*      [LABORATORY  ▼]            │
│  ACTIVITY TYPE:*     [GENERAL LAB ▼]            │
│  SUBACTIVITY TYPE:                   ▼          │
│  ORDER ENTRY FORMAT:*                           │
│                                                 │
│     [CLEAR]  [COPY FROM...]  [ADD ORDERABLE]    │
└─────────────────────────────────────────────────┘
```

REVIEW THE NEW ORDERABLE ITEMS YOU HAVE ADDED AND CLICK OK WHEN YOU ARE FINISHED.

NEW ORDERABLE ITEMS

| LONG DESCRIPTION | NAME (PRIMARY SYNONYM) | DEPARTMENT NAME | CATALOG TYPE | ACTIVITY TYPE | SUBACTIVITY TYPE |
|---|---|---|---|---|---|

[REMOVE] [EDIT]

[OK] [CANCEL] — 2710

METHOD FOR SELECTIVELY ASSOCIATING CONTENT ITEMS WITH PRE-CONFIGURED ALTERNATIVES BASED UPON DIRECTED USER INPUT

CROSS-REFERENCE TO RELATED APPLICATIONS

This application claims the benefit of U.S. Provisional Patent Application No. 60/788,559, filed Mar. 31, 2006, entitled "Automated Implementation of a Healthcare Information System." This application is related by subject matter to U.S. patent application Ser. No. 11/695,367, entitled "Method for Automated Configuration, Implementation and/or Maintenance of a Healthcare Information System," and U.S. patent application Ser. No. 11/695,362, entitled "Automated Configuration, Implementation and/or Maintenance of a Healthcare Information System," each of which is filed on even date herewith and incorporated herein by reference in its entirety.

BACKGROUND

Healthcare information systems are traditionally institutionally customized and require a tremendous amount of time and effort to configure and/or implement from ground level or convert from a different system. This is primarily because such systems are manually built which is a tedious process at best, generally taking several months and multiple in-person consultant visits to accomplish.

Accordingly, a method for configuring, implementing and/or maintaining a healthcare information system that diminishes the time and effort required would be desirable. Additionally, an automated system that utilizes existing sources of information for configuration, implementation and/or maintenance to alleviate some of the tedious nature of the process would be advantageous.

BRIEF SUMMARY

Embodiments of the present invention relate to computerized systems, methods and computer-readable media having computer-executable instructions embodied thereon, for configuring, implementing, and/or maintaining a customized healthcare information system. In embodiments, such configuring, implementing, and/or maintaining may include automated design and build of a customized healthcare information system from the ground level or may be an automated converting or updating process of a user's existing healthcare information system. The systems and methods of embodiments of the present invention utilize input from a number of information sources prior to initiation of configuration/implementation/maintenance to tailor or flex the process in a manner that is facility and/or personnel specific, thus alleviating solicitation of unnecessary information. Such information sources may include, by way of example only, one or more of facility- and personnel-specific content, facility and personnel profiles, help and knowledge assistance information, and pre-configured content. The more information to which the system has access for initiation and run of the configuration/implementation/maintenance process, the more tailored the process may be and, accordingly, the less time and effort will be required.

In embodiments, systems and methods of the present invention facilitate configuration, implementation, and/or maintenance of a healthcare information system through a series of screen displays designed to solicit pertinent information from a user wherein each subsequent screen display is selected based, at least in part, upon information extracted from one or more previously presented screen displays. In one embodiment, presentation of such screen displays is Web-based.

Accordingly, in one embodiment, the present invention relates to a computerized system for configuring, implementing and/or maintaining a customized healthcare information system. The system includes at least one user content component, a pre-configured content component, and an automated survey component. The at least one user content component includes information specific to at least one of a facility and personnel based upon which the customized healthcare information system is being configured, implemented and/or maintained. The pre-configured content component includes content pre-configured to be relevant in configuring, implementing and/or maintaining the customized healthcare information system. The automated survey component is configured to receive input from the at least one user content component and the pre-configured content component and to direct further input based upon the input received.

In an additional embodiment, the present invention relates to a computerized system for configuring, implementing and/or maintaining a customized healthcare information system that includes a pre-configured content component, an automated survey component, a survey-directed information store and a survey-learned data component. The pre-configured content component includes content pre-configured to be relevant in configuring, implementing and/or maintaining the customized healthcare information system. The automated survey component is configured to receive input from at least one user content component and the pre-configured content component to direct further input based upon the input received. The survey-directed information store is configured to receive and store survey-directed information from the automated survey component. The survey-learned data component is configured to extract at least a portion of the survey-directed information from the survey-directed information store and to input the extracted survey-directed information into the pre-configured content component.

In a further embodiment, the present invention relates to a computerized system for configuring, implementing and/or maintaining a customized healthcare information system. The system includes a pre-configured content component including content pre-configured to be relevant in configuring, implementing and/or maintaining the customized healthcare information system; a knowledge portal configured to access information assistance data; and an automated survey component configured to receive input from the pre-configured content component and the knowledge portal and to direct further input based upon the input received.

In an additional embodiment, the present invention relates to one or more computer-readable media having computer-executable instructions embodied thereon that, when executed, aid in configuring, implementing and/or maintaining a customized healthcare information system. The method includes receiving content specific to at least one of a facility and personnel based upon which the customized healthcare information system is being configured, implemented and/or maintained; receiving pre-configured content from a pre-configured content information store, the pre-configured content being pre-determined to be relevant in configuring, implementing and/or maintaining the customized healthcare information system; and utilizing at least a portion of the received facility- and personnel-specific content and the received pre-configured content to automate solicitation of directed user input.

Still further, embodiments of the present invention relate to computerized methods for configuring, implementing and/or maintaining a customized healthcare information system. The method includes receiving pre-configured content from a pre-configured information store, the pre-configured content being pre-determined to be relevant in configuring, implementing and/or maintaining the customized healthcare information system; receiving content specific to at least one of a facility and personnel based upon which the customized healthcare information system is being configured, implemented and/or maintained; utilizing at least a portion of the received facility- and personnel-specific content and the received pre-configured content to automate directed solicitation of user input; receiving directed input of user information; storing the user information in association with at least one information store; extracting at least a portion of the user information from the at least one information store; and inputting the extracted user information into the pre-configured content information store.

In an additional embodiment, the present invention relates to one or more computer-readable media having computer-executable instructions embodied thereon that, when executed, aid in configuring, implementing and/or maintaining a customized healthcare information system. The method includes receiving pre-configured content from a pre-configured content information store, the pre-configured content being pre-determined to be relevant in configuring, implementing and/or maintaining the customized healthcare information system; receiving input from a knowledge portal, the knowledge portal being configured to access informational assistance data; and utilizing at least a portion of the received pre-configured content and the received input from the knowledge portal to automate solicitation of directed user input.

In a further embodiment, the present invention relates to one or more computer-readable media having computer-executable instructions embodied thereon that, when executed, perform a method in a clinical environment for selectively associating content items with pre-configured alternatives based upon directed user input. The method comprises receiving a first content item; determining a plurality of pre-configured alternatives for association with the first content item, wherein each of the plurality of pre-configured alternatives is determined utilizing one or more of pre-configured content, facility- and personnel-specific content, a facility and personnel profile, and informational assistance data; presenting the plurality of pre-configured alternatives for user selection; receiving user selection of one of the plurality of pre-configured alternatives for association with the first content item; receiving a second content item; and determining at least one pre-configured alternative for association with the second content item, wherein the at least one-preconfigured alternative is a member of the plurality of pre-configured alternatives but is not the one of the plurality of pre-configured alternatives selected by the user for association with the first content item. In one embodiment, each of the first and second content items is a clinical orderable item.

In yet another embodiment, the present invention relates to a method in a clinical environment for selectively associating content items with pre-configured alternatives based upon directed user input. The method comprises receiving a plurality of content items; determining plurality of pre-configured alternatives for association with each of the plurality of content items, wherein each of the plurality of pre-configured alternatives is determined utilizing one or more of pre-configured content, facility- and personnel-specific content, a facility and personnel profile, and informational assistance data, and wherein a first of the plurality of pre-configured alternatives is determined for association with each of a first and a second of the plurality of content items; presenting at least the first of the plurality of content items for association with the first of the plurality of pre-configured alternatives; receiving user selection of the first of the plurality of pre-configured alternatives for association with the first of the plurality of content items; and presenting at least one pre-configured alternative for association with the second of the plurality of content items, wherein the first of the plurality of pre-configured alternatives is not presented. In one embodiment, each of the plurality of content items is a clinical orderable item.

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

BRIEF DESCRIPTION OF THE DRAWINGS

Embodiments of the present invention are described in detail below with reference to the attached drawing figures, wherein:

FIG. 8 is a screen display of an exemplary user interface that may be displayed upon user selection of the "begin" selectable indicator of the "review previous orderable items" portion of FIG. 6, in accordance with an embodiment of the present invention;

FIG. 10 is a screen display of an exemplary user interface that may be displayed upon selection of the "begin" selectable indicator of the "exact name matches" portion of FIG. 9, in accordance with an embodiment of the present invention;

FIG. 12 is a screen display of an exemplary user interface that may be displayed upon selection of the "begin" selectable indicator of the "one-to-one matches" portion of FIG. 11, in accordance with an embodiment of the present invention;

Figure 13:
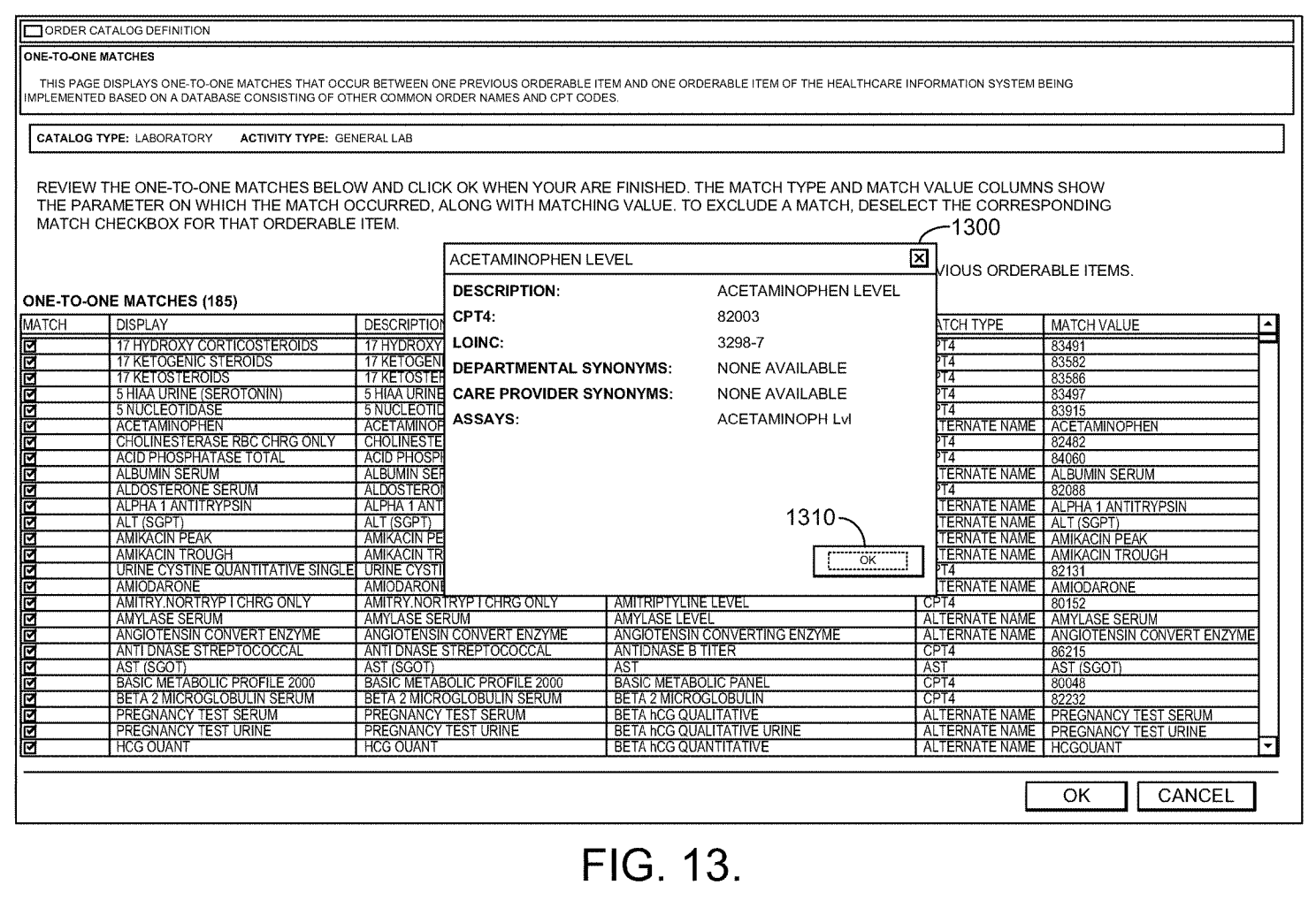

FIG. 13 is an exemplary screen display, in accordance with an embodiment of the present invention, illustrating the actual mapping of the "acetaminophen level" order catalog item of FIG. 12;

FIG. 15 is a screen display of an exemplary user interface that may be displayed upon selection of the "begin" selectable indicator of the "one-to-many matches" portion of FIG. 14, in accordance with an embodiment of the present invention;

FIG. 16 is a screen display, in accordance with an embodiment of the present invention, that may be displayed upon user selection of the "acetylcholine binding antibody" indicator in the one-to-many matches listing of FIG. 15 illustrating that two orderable item names in the healthcare information system being implemented matched to the previous orderable item name based on CPT codes;

FIG. 17 is a screen display, in accordance with an embodiment of the present invention, that may be displayed upon selection of the "acetylcholine receptor binding antibody" name in the name listing followed by the "OK" selectable indicator of FIG. 16;

FIG. 18 is a screen display, in accordance with an embodiment of the present invention, that may be displayed upon user selection of the "acetylcholine blocking antibody" indicator in the one-to-many matches listing of FIG. 17 illustrating that while previously two orderable item names in the healthcare information system being implemented matched to the previous orderable item name based on CPT codes, one such name has been assigned to another orderable item (in the screen display of FIG. 16) and, thus, only the remaining name is available;

FIG. 19 is a screen display, in accordance with an embodiment of the present invention, that may be displayed upon selection of the "acetylcholine receptor blocking antibody" name in the name listing followed by the "OK" selectable indicator of FIG. 18;

FIG. 21 is a screen display of an exemplary user interface that may be displayed upon selection of the "begin" selectable indicator of the "manual matches" portion of FIG. 20, in accordance with an embodiment of the present invention;

FIG. 23 is a screen display of an exemplary user interface that may be displayed upon selection of the "begin" selectable indicator of the "unmatched previous orderable items" portion of FIG. 22, in accordance with an embodiment of the present invention;

FIG. 25 is a screen display of an exemplary user interface that may be displayed upon selection of the "begin" selectable indicator of the "unmatched orderable items" portion of FIG. 24, in accordance with an embodiment of the present invention;

FIG. 27 is a screen display of an exemplary user interface that may be displayed upon selection of the "add orderable" selectable indicator of the "add new orderable items" portion of FIG. 26, in accordance with an embodiment of the present invention.

DETAILED DESCRIPTION

The subject matter of the present invention is described with specificity herein to meet statutory requirements. However, the description itself is not intended to limit the scope of this patent. Rather, the inventors have contemplated that the claimed subject matter might also be embodied in other ways, to include different steps or combinations of steps similar to the ones described in this document, in conjunction with other present or future technologies. Moreover, although the terms "step" and/or "block" may be used herein to connote different elements of methods employed, the terms should not be interpreted as implying any particular order among or between various steps herein disclosed unless and except when the order of individual steps is explicitly described.

Embodiments of the present invention relate to computerized systems, methods and computer-readable media having computer-executable instructions embodied thereon, for configuring, implementing, and/or maintaining a customized healthcare information system. In embodiments, such configuring, implementing, and/or maintaining may include automated design and build of a customized healthcare information system from the ground level or may be an automated converting or updating process of a user's existing healthcare information system. The systems and methods of embodiments of the present invention utilize input from a number of information sources prior to initiation of configuration/implementation/maintenance to tailor or flex the process in a manner that is facility and/or personnel specific, thus alleviating solicitation of unnecessary information. Such information sources may include, by way of example only, one or more of facility- and personnel-specific content, facility and personnel profiles, help and knowledge assistance information, and pre-configured content. The more information to which the system has access for initiation and run of the configuration/implementation/maintenance process, the more tailored the process may be and, accordingly, the less time and effort will be required.

Figure 1:
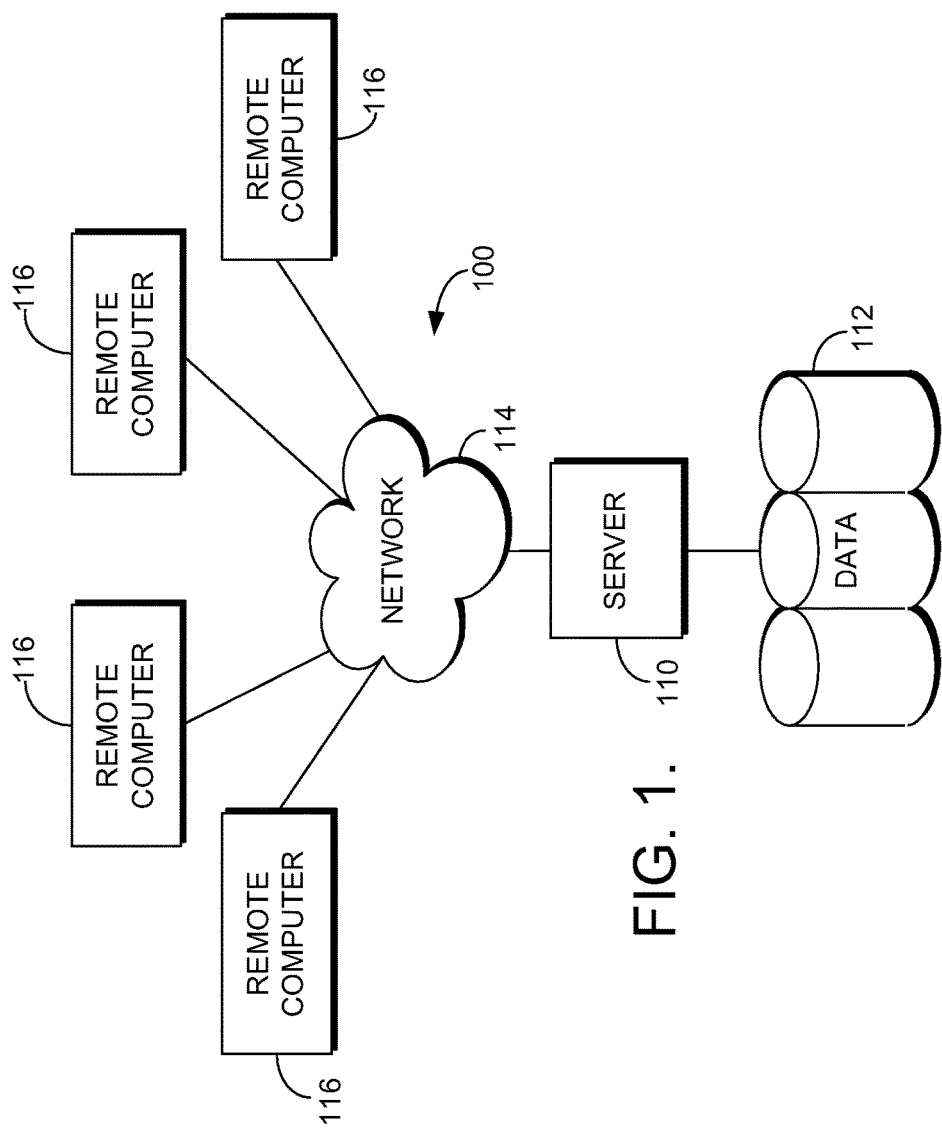
FIG. 1 is a block diagram of an exemplary computing environment suitable for use in implementing embodiments of the present invention.

Referring to the drawings in general, and initially to FIG. 1 in particular, an exemplary computing system environment, for instance, a medical information computing system, on which embodiments of the present invention may be implemented is illustrated and designated generally as reference numeral 100. It will be understood and appreciated by those of ordinary skill in the art that the illustrated medical information computing system environment 100 is merely an example of one suitable computing environment and is not intended to suggest any limitation as to the scope of use or functionality of the invention. Neither should the medical information computing system environment 100 be interpreted as having any dependency or requirement relating to any single component/module or combination of components/modules illustrated therein.

Embodiments of the present invention may be operational with numerous other general purpose or special purpose computing system environments or configurations. Examples of well-known computing systems, environments, and/or configurations that may be suitable for use with embodiments of the present invention include, by way of example only, personal computers, server computers, handheld or laptop devices, multiprocessor systems, microprocessor-based systems, set top boxes, programmable consumer electronics, network PCs, minicomputers, mainframe computers, distributed computing environments that include any of the above-mentioned systems or devices, and the like.

Embodiments of the present invention may be described in the general context of computer-executable instructions, such as program modules, being executed by a computer. Generally, program modules include, but are not limited to, routines, programs, objects, components, and data structures that perform particular tasks or implement particular abstract data types. The present invention may also be practiced in distributed computing environments where tasks are performed by remote processing devices that are linked through a communications network. In a distributed computing environment, program modules may be located in local and/or remote computer storage media including, by way of example only, memory storage devices.

With continued reference to FIG. 1, the exemplary medical information computing system environment 100 includes a general purpose computing device in the form of a server 110. Components of the server 110 may include, without limitation, a processing unit, internal system memory, and a suitable system bus for coupling various system components, including database cluster 112, with the server 110. The system bus may be any of several types of bus structures, including a memory bus or memory controller, a peripheral bus, and a local bus, using any of a variety of bus architectures. By way of example, and not limitation, such architectures include Industry Standard Architecture (ISA) bus, Micro Channel Architecture (MCA) bus, Enhanced ISA (EISA) bus, Video Electronic Standards Association (VESA) local bus, and Peripheral Component Interconnect (PCI) bus, also known as Mezzanine bus.

The server 110 typically includes, or has access to, a variety of computer readable-media, for instance, database cluster 112. Computer-readable media can be any available media that may be accessed by server 110, and includes volatile and nonvolatile media, as well as removable and non-removable media. By way of example, and not limitation, computer-readable media may include computer storage media and communication media. Computer storage media may include, without limitation, volatile and non-volatile media, as well as removable and non-removable media implemented in any method or technology for storage of information, such as computer-readable instructions, data structures, program modules, or other data. In this regard, computer storage media may include, but is not limited to, RAM, ROM, EEPROM, flash memory or other memory technology, CD-ROM, digital versatile disks (DVDs) or other optical disk storage, magnetic cassettes, magnetic tape, magnetic disk storage, or other magnetic storage device, or any other medium which can be used to store the desired information and which may be accessed by the server 110. Communication media typically embodies computer-readable instructions, data structures, program modules, or other data in a modulated data signal, such as a carrier wave or other transport mechanism, and may include any information delivery media. As used herein, the term "modulated data signal" refers to a signal that has one or more of its attributes set or changed in such a manner as to encode information in the signal. By way of example, and not limitation, communication media includes wired media such as a wired network or direct-wired connection, and wireless media such as acoustic, RF, infrared, and other wireless media. Combinations of any of the above also may be included within the scope of computer-readable media.

The computer storage media discussed above and illustrated in FIG. 1, including database cluster 112, provide storage of computer-readable instructions, data structures, program modules, and other data for the server 110.

The server 110 may operate in a computer network 114 using logical connections to one or more remote computers 116. Remote computers 116 may be located at a variety of locations in a medical or research environment, for example, but not limited to, clinical laboratories, hospitals and other inpatient settings, veterinary environments, ambulatory settings, medical billing and financial offices, hospital administration settings, home health care environments, and clinicians' offices. The remote computers 116 may also be physically located in non-traditional medical care environments so that the entire healthcare community may be capable of integration on the network 114. The remote computers 116 may be personal computers, servers, routers, network PCs, peer devices, other common network nodes, or the like, and may include some or all of the elements described above in relation to the server 110. The devices can be personal digital assistants or other like devices.

Exemplary computer networks 114 may include, without limitation, local area networks (LANs) and/or wide area networks (WANs). Such networking environments are commonplace in offices, enterprise-wide computer networks, intranets, and the Internet. When utilized in a WAN networking environment, the server 110 may include a modem or other means for establishing communications over the WAN, such as the Internet. In a networked environment, program modules or portions thereof may be stored in the server 110, in the database cluster 112, or on any of the remote computers 116. For example, and not by way of limitation, various application programs may reside on the memory associated with any one or more of the remote computers 116. It will be appreciated by those of ordinary skill in the art that the network connections shown are exemplary and other means of establishing a communications link between the computers (e.g., server 110 and remote computers 116) may be utilized.

In operation, a user may enter commands and information into the server 110 or convey the commands and information to the server 110 via one or more of the remote computers 116 through input devices, such as a keyboard, a pointing device (commonly referred to as a mouse), a trackball, or a touch pad. Other input devices may include, without limitation, microphones, satellite dishes, scanners, or the like. Commands and information may also be sent directly from a remote healthcare device to the server 110. In addition to a monitor, the server 110 and/or remote computers 116 may include other peripheral output devices, such as speakers and a printer.

Although many other internal components of the server 110 and the remote computers 116 are not shown, those of ordinary skill in the art will appreciate that such components and their interconnection are well known. Accordingly, additional details concerning the internal construction of the server 110 and the remote computers 116 are not further disclosed herein.

Although methods and systems of embodiments of the present invention are described as being implemented in a WINDOWS operating system, operating in conjunction with an Internet-based system, one of ordinary skill in the art will recognize that the described methods and systems can be implemented in any system supporting the automated configuration, implementation and/or maintenance of a healthcare information system. As contemplated by the language above, the methods and systems of embodiments of the present invention may also be implemented on a stand-alone desktop, personal computer, or any other computing device used in a healthcare environment or any of a number of other locations.

Figure 2:
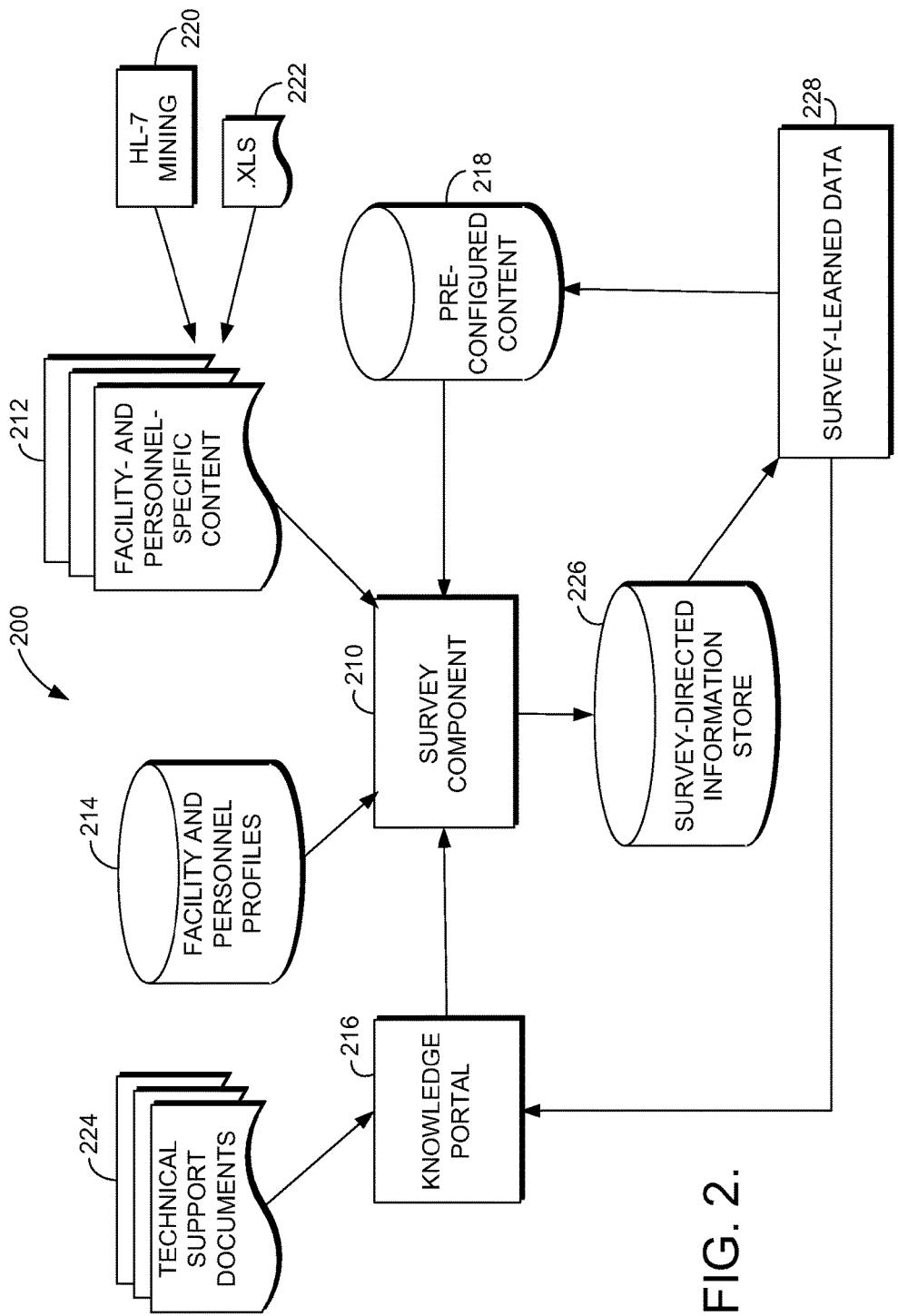
FIG. 2 is a block diagram of an exemplary system architecture for use in implementing embodiments of the present invention.

As previously mentioned, the present invention relates to computerized systems and methods for the automated configuration, implementation and/or maintenance of a healthcare information system. Turning to FIG. 2, an exemplary system architecture for use in implementing embodiments of the present invention is illustrated and designated generally as reference numeral 200. It will be understood and appreciated by those of ordinary skill in the art that the overall system architecture 200 shown in FIG. 2 is merely an example of one suitable system architecture and is not intended to suggest any limitation as to the use or functionality of the present invention. Neither should the overall system architecture 200 be interpreted as having any dependency or requirement related to any single component/module or combination of components/modules illustrated therein.

System 200 includes a survey component 210 configured to receive input from a number of content components. Such content components include a facility- and personnel-specific content component 212, a facility and personnel profile content component 214, a knowledge portal 216 and a pre-configured content component 218. It will be understood and appreciated by those of ordinary skill in the art that the number and nature of the inputs into the survey component 210 are merely exemplary and are not intended to limit the scope of embodiments of the present invention in any way.

The facility- and personnel-specific content component 212 includes localized data derived from the particular facility, group of facilities, facility network, facility portion, or the like that desires to configure, implement and/or maintain the customized healthcare information system. Such localized data may include, by way of example only, clinician and other personnel lists, the physical address of one or more healthcare locations operated by the user, the facility organization and design of one or more healthcare locations operated by the user, patient profiles, user preferences, user-specific orderable items and any associated aliases and/or collection requirements, work routing preferences, and the like. Basically, the localized data includes any data that is unique to the particular facility, facility portion, facility group, etc. that desires to configure, implement and/or maintain the healthcare information system in question and that cannot be estimated or derived absent specific input or interaction with such data. Such data may be input into the facility- and personnel-specific content component 212 from a variety of sources including, by way of example only, data collected through Health Level 7 (HL-7) mining 220 of the facility's existing healthcare information system and/or data collected through facility- or personnel-specific tables or spreadsheets 222, which may be manually or automatically populated. Facility- and personnel-specific content component 212 is generally utilized in situations where the facility (facility portion, facility group, or the like) has an existing healthcare information system and desires to have such system updated or modified or to have a different healthcare information system configured and/or implemented. If necessary, upon extraction of data from the facility- and personnel-specific content component 212, such data is formatted to the requirements of the survey component 210 and input therein.

Facility and personnel profile component 214 includes high-level data about the nature of the facility (facility portion, facility group, etc.) and/or associated personnel. For instance, the facility and personnel profile component 214 may include data regarding what particular solutions the facility (facility portion, facility group, etc.) desires to have configured, implemented and/or maintained in its healthcare information system or data regarding what type of healthcare facility (facilities, facility portions, etc.) being operated (e.g., a children's hospital, an academic hospital, or the like). Such information is typically collected during cursory conversations or meetings, or preliminary fact-finding scenarios with respect to a particular facility (or the like) and input into the facility and personnel profile component 214. If necessary, upon extraction of data from the facility and personnel profile component 214, such data is formatted to the requirements of the survey component 210 and input therein.

Knowledge portal 216 is configured to access and/or provide informational assistance data that will be available during configuration, implementation and/or maintenance of the healthcare information system, such data generally being presented in a natural language format. For instance, the knowledge portal 216 may include, by way of example only and not limitation, instruction on how to use the survey component 210, instruction on how to use a particular screen display presented during use of the survey component 210, information regarding the reasoning for attempting to extract a particular piece of data from a user, data supporting the ramifications of selecting one option over another (including real-life examples), definitions of terms, frequently asked questions, graphical displays, work charts, representations of front-end applications, and the like. Such information may be input into the knowledge portal 216 from a variety of sources including, by way of example only and not limitation, extraction from technical support documents 224. In this regard, data may not simply be transferred from the technical support documents 224 into the knowledge portal 216 but may be converted from technical language to a more natural, user-friendly language upon input into the knowledge portal 216.

The knowledge portal 216 may additionally include data input from survey-learned data component 228, which component is more fully discussed herein below. If necessary, upon extraction of data from the knowledge portal 216, such data is formatted to the requirements of the survey component 210 and input therein.

Pre-configured content component 218 includes content that is pre-configured to be relevant in configuring, implementing and/or maintaining the desired for building the healthcare information system in question. In this regard, the pre-configured content may be based, at least in part, upon the preferences and/or regulations of a particular healthcare system, the preferences and/or regulations of healthcare systems in a particular country or region, or the like. The pre-configured content includes survey-specific tables that contain all of the options a user/facility may desire with respect to healthcare information system configuration, implementation and/or maintenance. The pre-configured content further includes information regarding typical healthcare information system configurations for, e.g., particular types of healthcare facilities, and the like. In this regard, if a facility (facility group, facility portion, or the like) does not have an existing healthcare information system and, accordingly, such system is being configured and/or implemented from the ground level, such configuration/implementation may be seeded with data derived from such pre-configured, typical configurations as opposed to seeded with facility- and personnel-specific data input from the facility- and personnel-specific content component 212 as would be the case if the user had an existing healthcare information system. In one embodiment, content from each of the pre-configured content component 218 and the facility- and personnel-specific content component 212 is input into the survey component 210 for utilization in configuring, implementing and/or maintaining a healthcare information system. Any and all such variations and combinations thereof are contemplated to be within the scope of embodiments of the present invention.

Data concerning typical healthcare information system configurations and preferences may be derived, at least in part, from survey-learned information stored in association with survey-learned data component 228. Survey-learned data component 228 includes data that has been mined or extracted from the survey-directed information store 226, which information store contains data associated with each configuration, implementation and/or maintenance of the healthcare information system. Thus, with respect to the healthcare information system being configured/implemented/maintained, the survey-directed information store 226 includes clinical or common best practices, facilities data, and the like. The survey-directed information store is more fully discussed herein below.

Survey component 210 is configured not only to receive various inputs as described above, but also to present a plurality of screen displays from which a user may input information to customize the healthcare information system being configured, implemented and/or maintained. Such screen displays may be presented on any type of computing device, for instance, a user's personal computer, desktop computer, laptop computer, handheld device, consumer electronic device, and the like. It should be noted, however, that the invention is not limited to implementation on such computing devices, but may be implemented on any of a variety of different types of computing devices within the scope of embodiments of the present invention. Typically, presentation of the screen displays comprises displaying the screen displays on a display device associated with a computing device as discussed above. However, other types of presentation, such as audible presentation, may also be provided within the scope of embodiments of the present invention.

The screen displays which are presented by the survey component 210 are selected based upon at least a portion of the information input into the survey component 210. Thus, the screen displays that are presented by the survey component 210 are flexed based upon the information already available to the survey component 210 prior to user interaction with the screen displays. Accordingly, the screen displays that are available for user input and interaction will vary for each facility (facility group, facility portion, etc.) configuring, implementing and/or maintaining the healthcare information system in question. Additionally, as the user interacts with each of the screen displays presented and inputs additional information into the system, each subsequent screen display is selected for presentation taking into account that information. In this way, the healthcare information system configuration, implementation and/or maintenance process is customized for each facility (facility group, facility portion, and the like), significantly decreasing the time and effort such configuration/implementation/maintenance may take. Customization of the healthcare information system and exemplary user-directed screen displays are discussed more fully herein below with reference to FIGS. 4-27.

The survey component 210 is further configured to output facility- and personnel-specific data to a survey-directed information store 226 once information has been input, and presented to and customized by a user. Only that information which was selected by and/or customized by the user is output to the information store 226 and, as such, the information in the information store 226 is both facility- and personnel-specific and survey-directed. The information in the survey-directed information store 226 is subsequently available for mining and extraction by the survey-learned data component 228 and, if desired, input into the pre-configured content component 218 and/or knowledge portal 216. In this way, the healthcare information system 200 gets "smarter" with each configuration/implementation/maintenance run, that is, it has additional information available to it that allows it to further customize and direct the user through the process.

Figure 3:
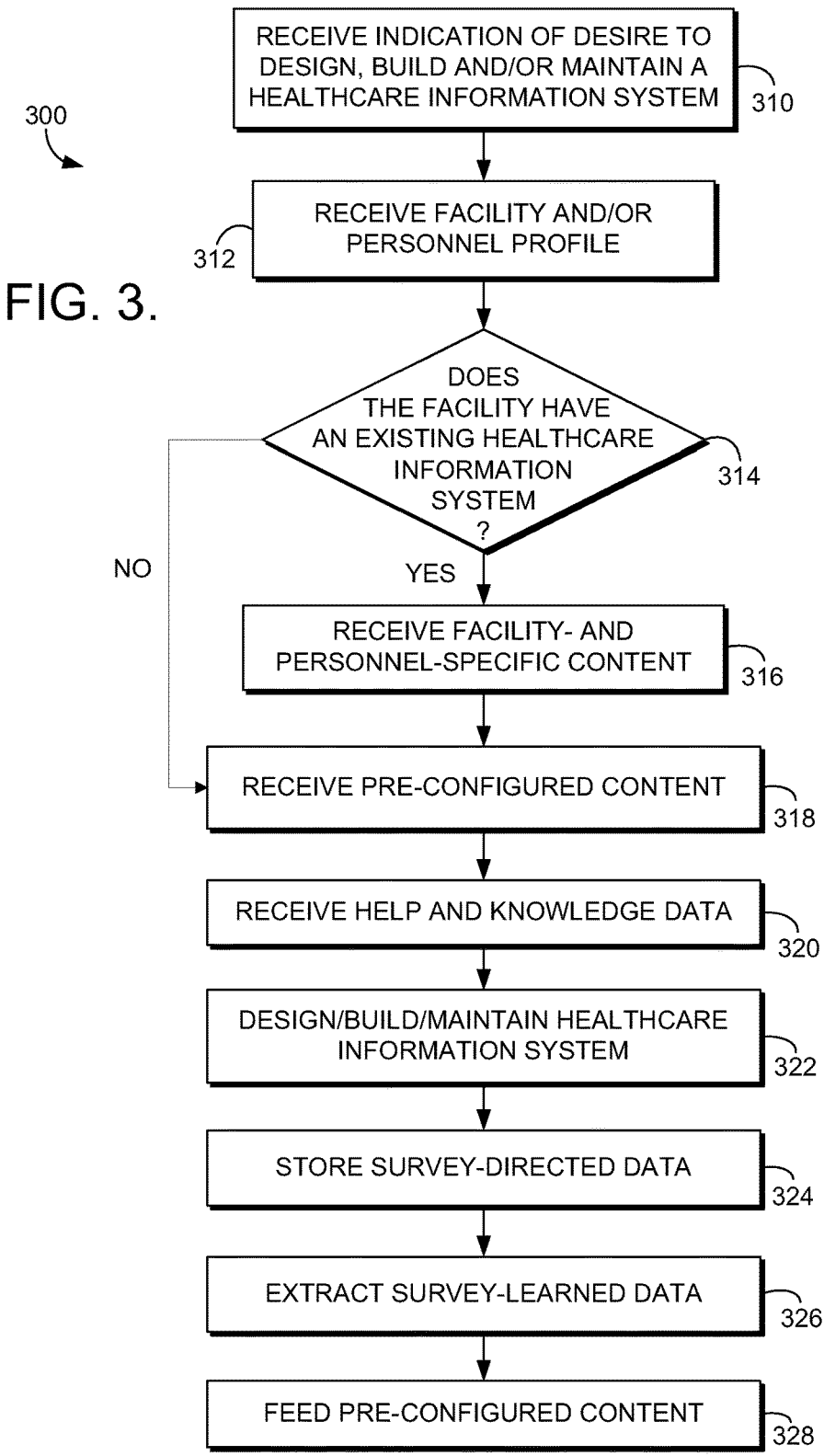
FIG. 3 is a flow diagram, in accordance with an embodiment of the present invention, illustrating a method for configuring, implementing and/or maintaining a healthcare information system.

Turning to FIG. 3, a flow diagram is illustrated which shows an exemplary method 300 for automated configuration, implementation and/or maintenance of a healthcare information system, in accordance with an embodiment of the present invention. Initially, as indicated at block 310, an indication that a user associated with a facility (group of facilities, facility portion, or the like) desires to configure, implement or maintain a healthcare information system is received. Such indication may be received, for instance, upon user selection of a "survey" icon present on the desktop of a display associated with the user's computing device. Subsequently, an accessible facility and/or personnel profile for the facility (group of facilities, facility portion, etc.) associated with the user is received, as indicated at block 312. Such facility and/or personnel profile may be received, for instance, by survey component 210 from facility and personnel profile component 214 of FIG. 2.

Next, it is determined whether or not the facility(ies) associated with the user has an existing healthcare information system. This is indicated at block 314. Such determination may be made, for instance, by survey component 210 of the system architecture 200 of FIG. 2. If it is determined that the facility(ies) associated with the user does have an existing healthcare information system, facility- and/or personnel-specific content derived from the existing healthcare information system is subsequently received, as indicated at block 316. Such facility- and personnel-specific content may be received, for instance, by survey component 210 from facility- and personnel-specific content component 212 of FIG. 2.

Subsequently, or if it is determined at block 314 that the facility (facilities, facility portion, or the like) associated with the user does not have an existing healthcare information system, pre-configured content that is pre-configured to be relevant in configuring, implementing and/or maintaining the healthcare information system is received. This is indicated at block 318. Such pre-configured content may be received, for instance, by survey component 210 from pre-configured content component 210 of FIG. 2. Subsequently, prior to, or simultaneously, help and knowledge data is received, as indicated at block 320. Such help and knowledge data may be received, by way of example only and not limitation, by survey component 210 of FIG. 2 from knowledge portal 216.

It will be understood and appreciated by those of ordinary skill in the art that the order of steps 310, 312, 314, 316, 318, and 320 is presented by way of example only and is not intended to limit the scope of the invention in any way. Input from each of the various sources of information may be received simultaneously, consecutively and/or in any order. Additionally, information from any one or more of the various information sources may be received within embodiments hereof. All such variations are contemplated to be within the scope of embodiments of the present invention.

Once all available information has been received, the healthcare information system is configured, implemented, updated, and/or maintained as indicated at block 322. Such configuration/implementation/maintenance may be conducted, for instance, utilizing a series of screen displays presented to the user as described hereinabove. (One exemplary series of screen displays for implementing general lab order catalog functionality is more fully described below with reference to FIGS. 4-27.) Once the configuration, implementation and/or maintenance run is complete, the facility- and personnel-specific, survey-directed information is stored, as indicated at block 324. Such information may be stored, for instance, in the facility- and personnel-specific, survey-directed information store 226 (or database) of the system architecture 200 of FIG. 2.

If desired, the survey-learned data may be mined, extracted, or otherwise retrieved for utilization in future implementations, updates and/or maintenance of the healthcare information system. This is indicated at block 326. In one embodiment, the survey-learned data may be extracted by survey-learned data component 228 from the facility- and personnel-specific, survey-directed information store 226 of FIG. 2 utilizing data mining techniques known to those of ordinary skill in the art. Subsequently, as indicated at block 328, the survey-learned data may be fed, for instance, in the pre-configured content component 218 and/or the knowledge portal component 216 of FIG. 2. In this way, the system improves, or becomes "smarter," with each consecutive run.

Turning now to FIGS. 4-27, a series of exemplary screen displays for reconciling a general laboratory order catalog from a previous healthcare information system with the order catalog for the healthcare information system being configured, implemented and/or maintained is provided. It will be understood and appreciated by those of ordinary skill in the art that the series of screen displays presented in FIGS. 4-27 is exemplary in nature and is not intended to limit the scope of the present invention in any way.

Figure 4:
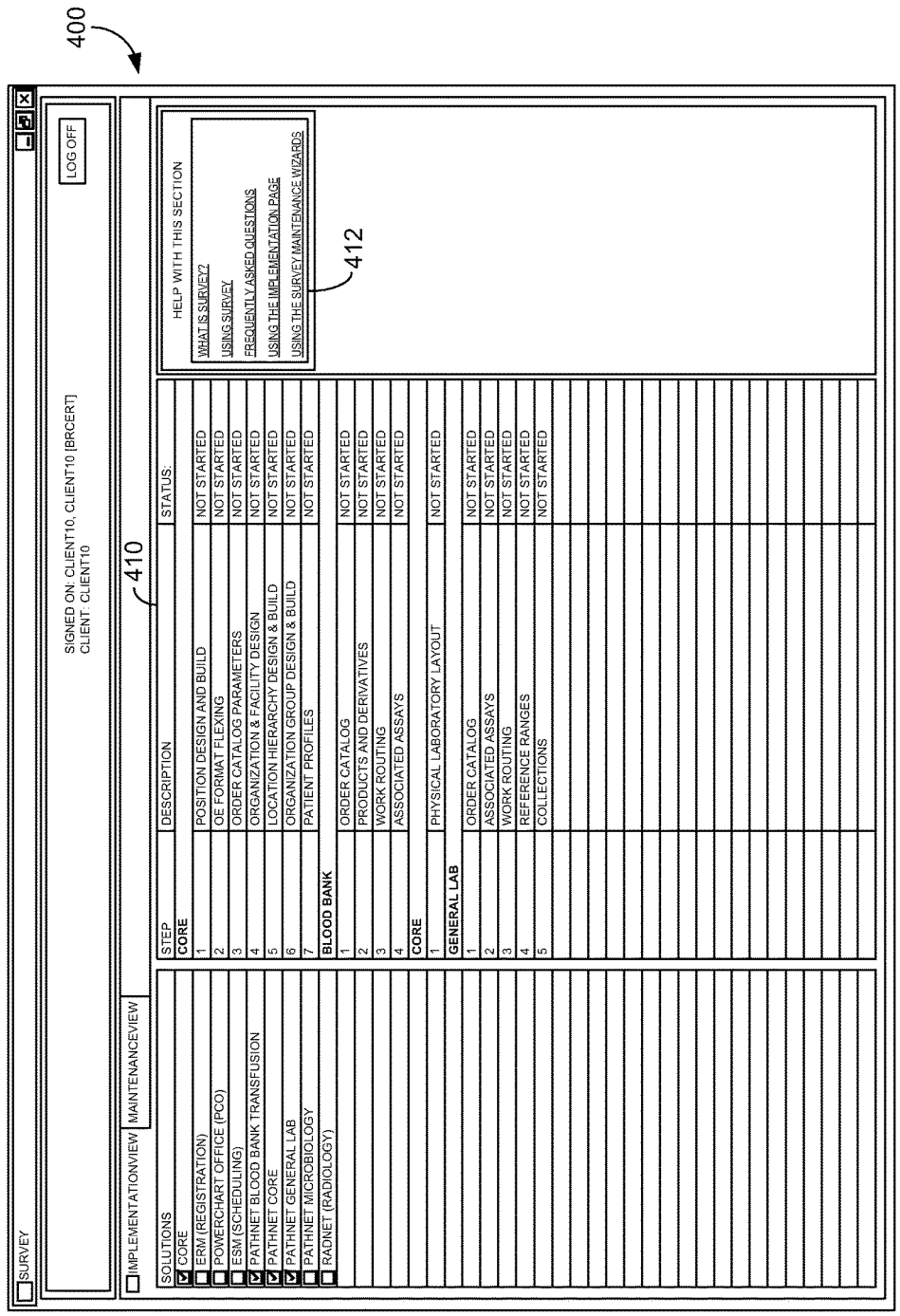
FIG. 4 is a screen display of an exemplary user interface illustrating a number of user-directed wizards that may be run in order to set up and/or modify particular functionalities upon configuration, implementation and/or maintenance of a healthcare information system, in accordance with an embodiment of the present invention.

With initial reference to FIG. 4, an exemplary user interface illustrating a number of user-directed wizards that may be run in order to configure and/or modify particular functionalities upon configuration, implementation and/or maintenance of a healthcare information system is illustrated and designated generally as reference numeral 400. User interface 400 includes an available wizard portion 410 and a help and knowledge portion 412. The available wizard portion 410 is configured to display selectable links for each wizard that is available to the user for implementation. The wizards shown in the available wizard portion 410 are selected based upon the information input into, for instance, the survey component 210 of the system architecture 200 of FIG. 2. In this regard, the wizards shown are only those which pertain to the facility or facilities (or facility portion) associated with the user and relate to areas or functionalities for which additional information needs to be solicited from the user for configuration, implementation and/or maintenance to be complete. As such, the available wizard portion 410 of FIG. 4 will display different wizards for each facility (facility group, facility portion, or the like) initiating configuration, implementation, and/or maintenance of the healthcare information system.

The help and knowledge portion 412 of the user interface 400 is configured to display one or more selectable links to additional information that may be of use to the user in completing the healthcare information system configuration, implementation and/or maintenance. Such additional information may be derived, for instance, from the knowledge portal 216 of the system architecture 200 of FIG. 2.

Figure 5:
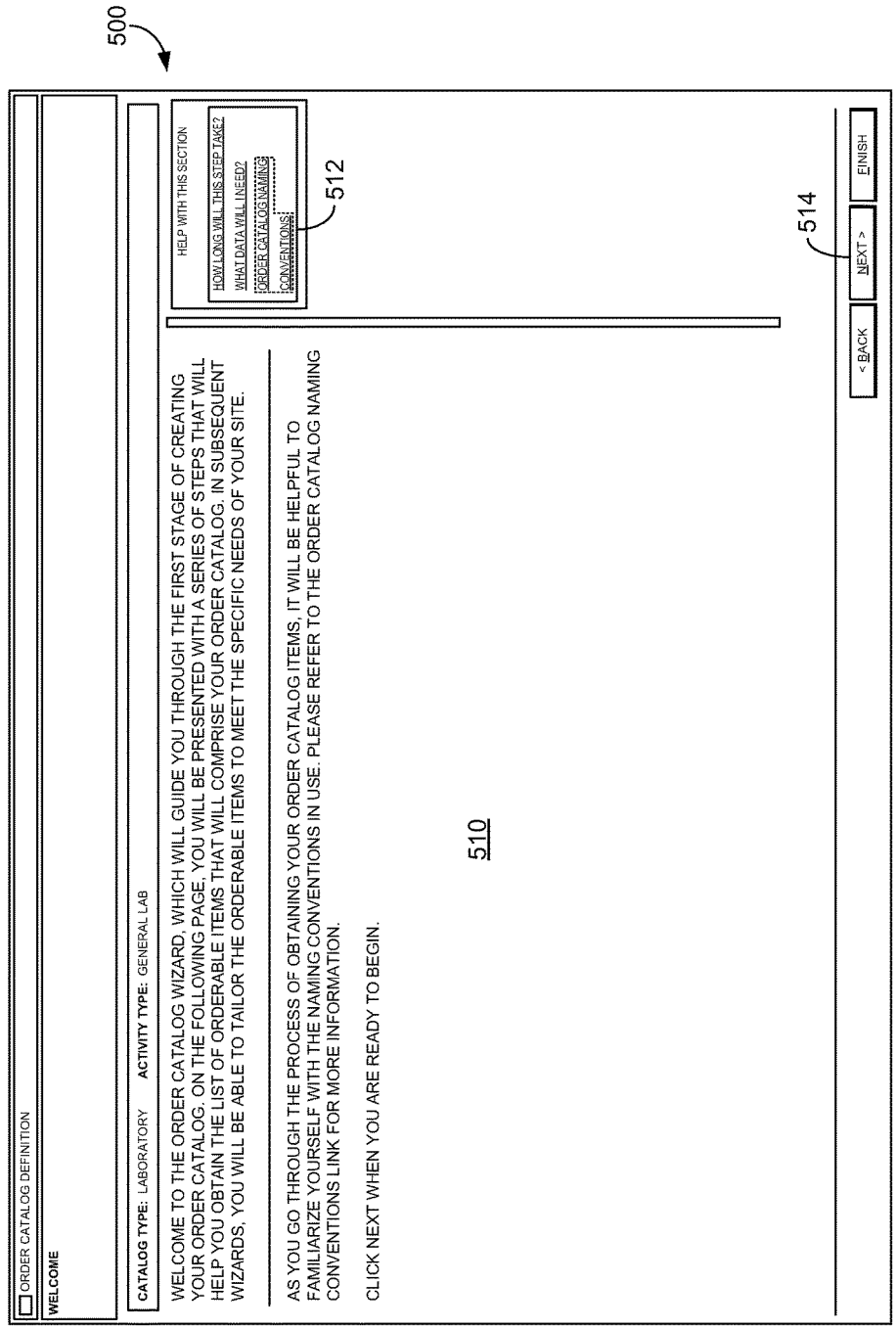
FIG. 5 is a screen display, in accordance with an embodiment of the present invention, of an exemplary user interface that may be displayed upon selection of the "order catalog" user-directed wizard listed in the available wizard portion of FIG. 4.
Figure 6:
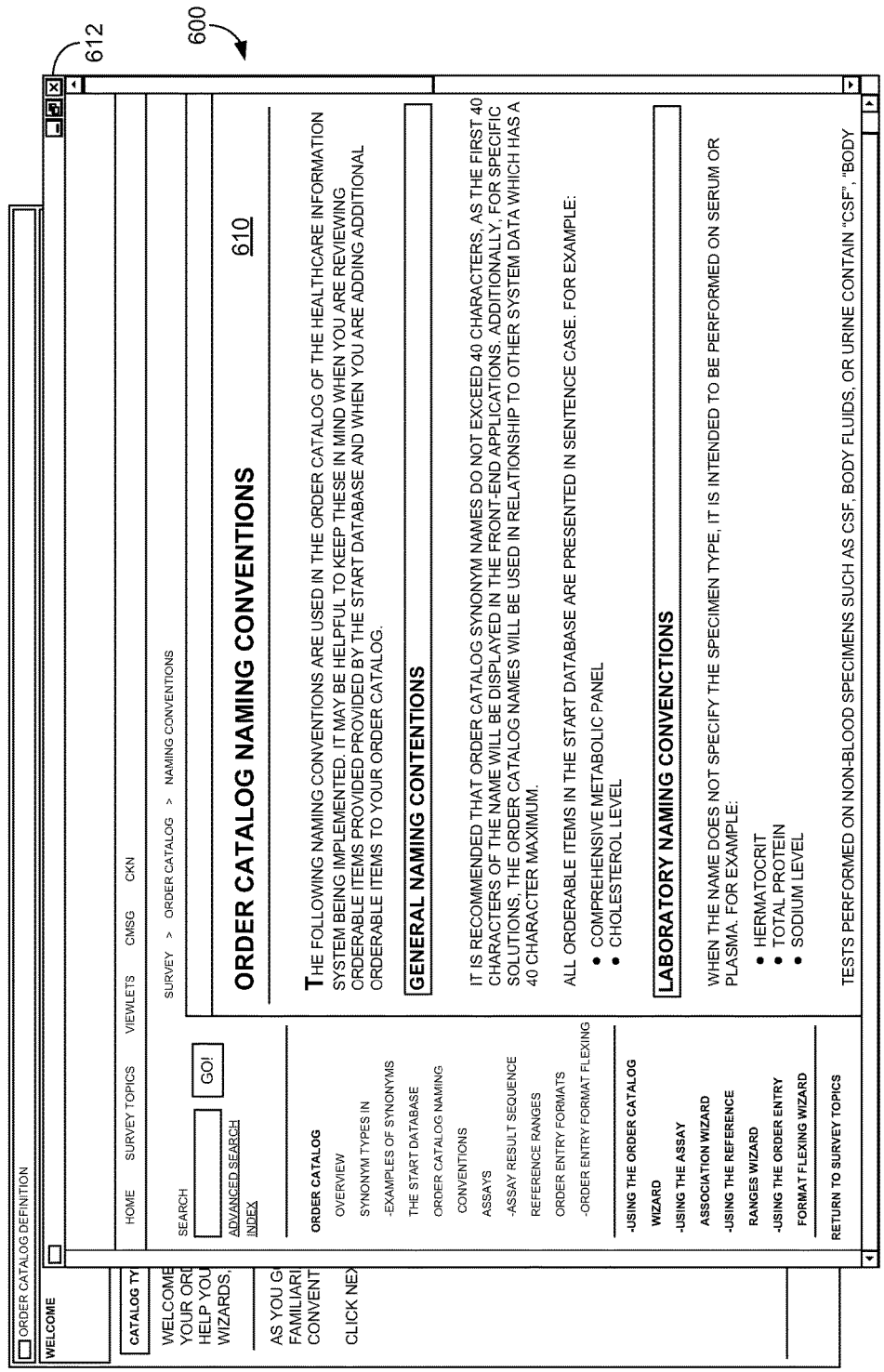
FIG. 6 is a screen display of an exemplary user interface that may be displayed upon user selection of the "order catalog naming conventions" selectable indicator in the help and knowledge portion of FIG. 5.

Referring now to FIG. 5, an exemplary user interface that may be displayed upon selection of the "order catalog" user-directed wizard listed in the available wizard portion 410 of user interface 400 (FIG. 4) is illustrated and designated generally as reference numeral 500. User interface 500 includes an informational portion 510 and a help and knowledge portion 512. The information portion 510 is configured to display instructional information to the user that pertains to the selected wizard, i.e., the general laboratory order catalog wizard. The information portion 512 is further configured to display instructional information regarding next steps the user needs to take to proceed with configuration, implementation and/or maintenance of the selected portion of the healthcare information system, (i.e., "click next when you are ready to begin").

As with the help and knowledge portion 412 of FIG. 4, the help and knowledge portion 512 of FIG. 5 is configured to display one or more selectable links to additional information that may be of use to the user in completing the healthcare information system configuration, implementation and/or maintenance, in this instance, the general laboratory order catalog wizard. Such additional information may be derived, for instance, from knowledge portal 216 of the system architecture 200 of FIG. 2. In this regard, if the user were to select the "order catalog naming conventions" selectable link displayed in the help and knowledge portion 512, the screen display 600 of FIG. 6 may be presented.

User interface 600 includes an informational portion 610 configured to display the requested information in a natural language, user-friendly format. In the particular illustrated scenario, the informational portion 610 is configured to display information regarding the order catalog naming conventions that are associated with the healthcare information system being configured, implemented and/or maintained. Once the user has completed review of the information shown in the informational portion 610 of the user interface 600, a close indicator 612 may be selected and the user may be returned to the user interface 500 of FIG. 5.

Referring back to FIG. 5, user interface 500 additionally includes a selectable "next" indicator 514 which the user may select when the user is ready to initiate the general laboratory order catalog wizard. In this regard, selection of the "next" indicator 514 may initiate display of the user interface 700 of FIG. 7. User interface 700 includes a "review previous orderable items" display portion 710. As shown in display portion 710, the user is informed that upon initiation of this portion of the series of matching functionalities which comprise the order catalog implementation, the user will be directed to select orderable items that should be disregarded during the matching steps that occur throughout the remainder of the configuration, implementation and/or maintenance process. If the user desires to proceed with the order catalog implementation, the selectable "begin" indicator 712 may be selected.

Figure 7:
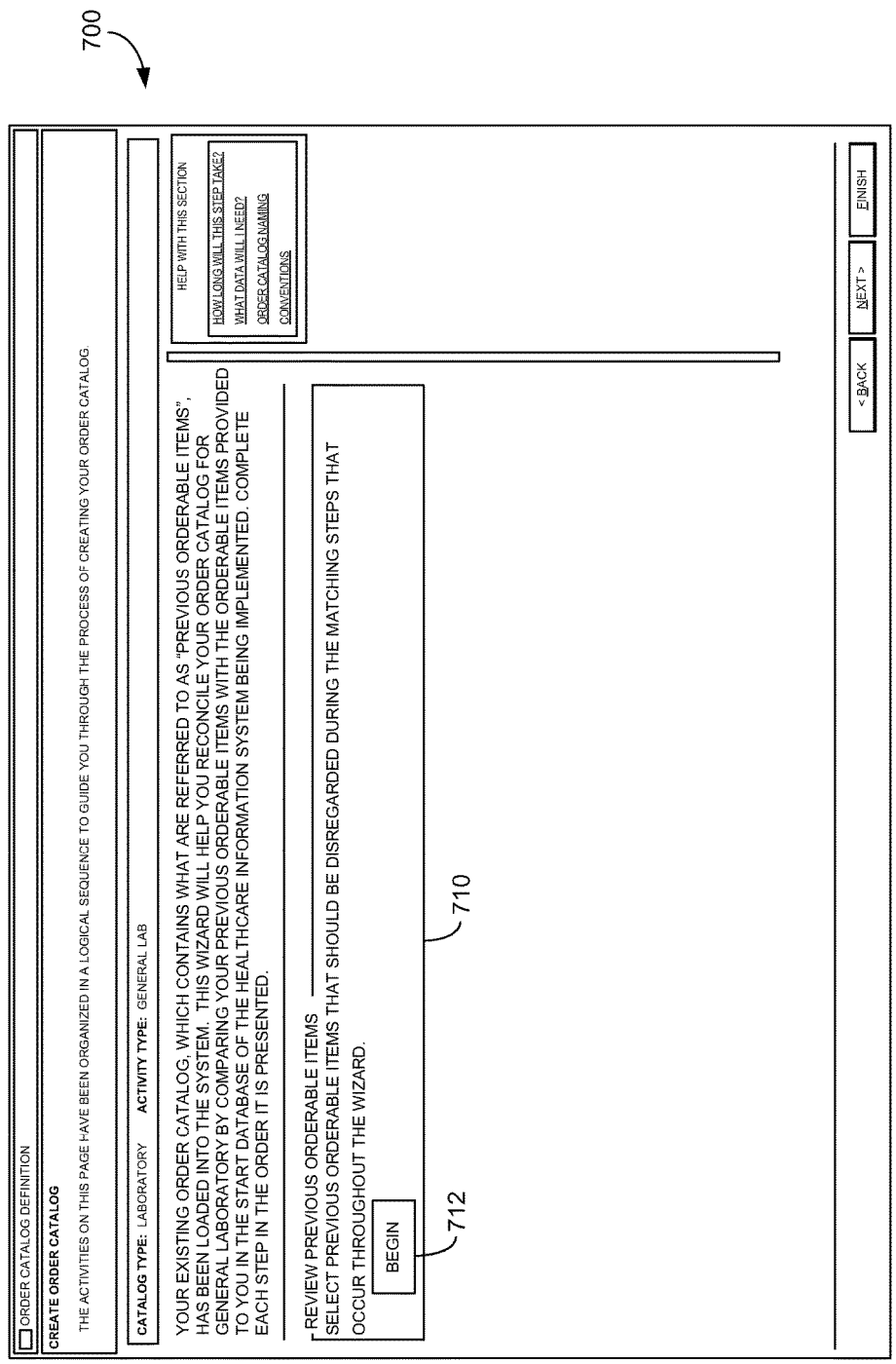
FIG. 7 is a screen display, in accordance with an embodiment of the present invention, of an exemplary user interface that may be displayed upon selection of the "next" selectable indicator of FIG. 5.

Turning now to FIG. 8, a screen display of an exemplary user interface 800 that may be displayed upon user selection of the "begin" selectable indicator 712 of the "review previous orderable items" portion 710 of FIG. 7 is provided. User interface 800 includes an informational portion 810 configured to display information informing the user that the intent of the order catalog wizard is to reconcile previous orderable items with the orderable items provided in the pre-configured content database of the healthcare information system being configured, implemented and/or maintained. During this step, the user is asked to identify any items on the list of orderable items from the previous healthcare information system that it desires to exclude from consideration. In effect, this step is providing the user with the opportunity to clean up and/or manipulate any data which did not import correctly into the system and/or which it does not desire to maintain in the new healthcare information system. Once the user has completed this portion of the reconciliation process, the user may select the selectable "OK" indicator 812 to move on to the next step.

Figure 9:
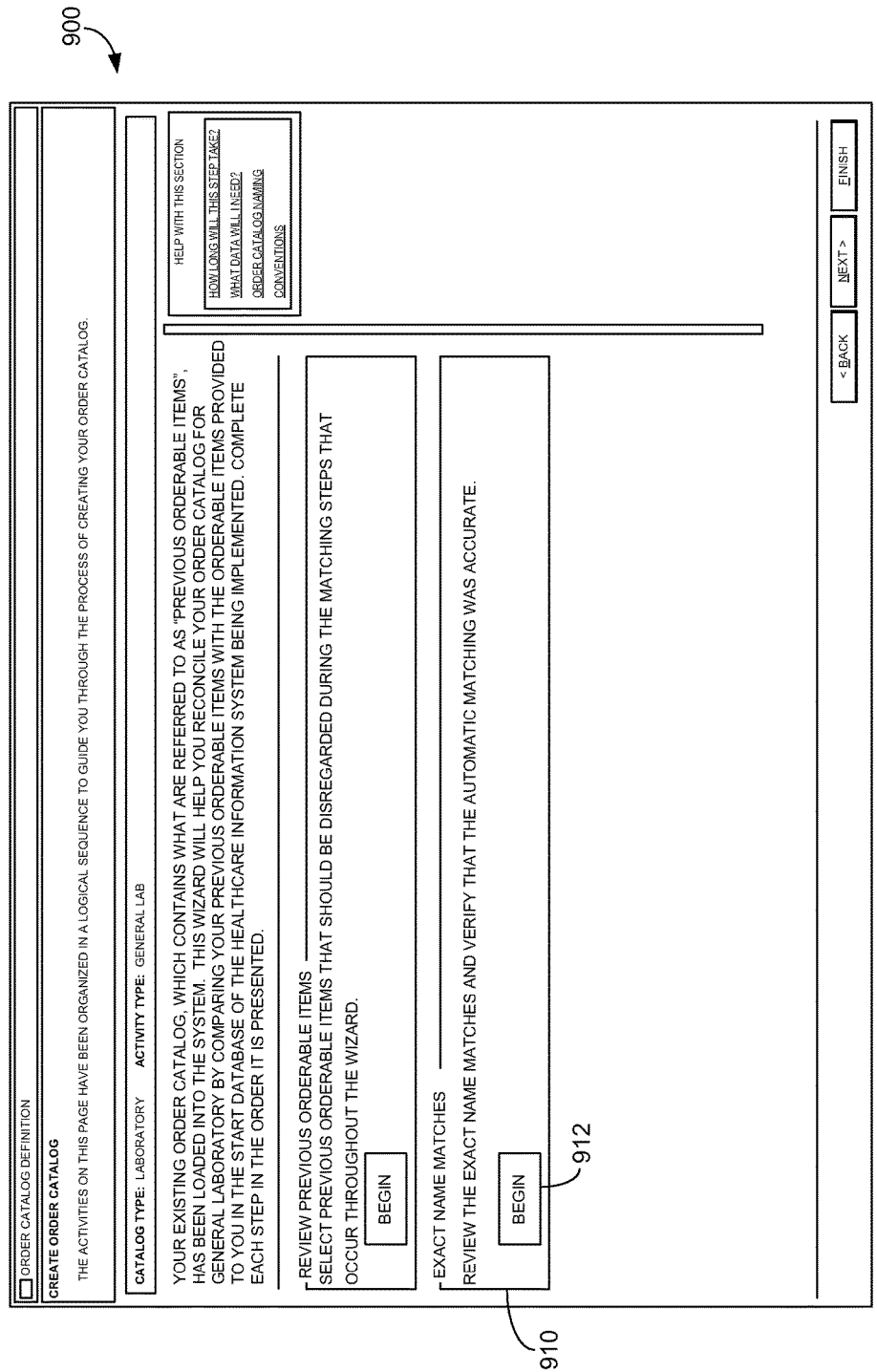
FIG. 9 is a screen display, in accordance with an embodiment of the present invention, of an exemplary user interface that may be displayed upon selection of the "OK" indicator of FIG. 8 illustrating that the next step in the series of order matching functionalities is an "exact name" matching functionality.

With reference to FIG. 9, a screen display of an exemplary user interface 900 that may be displayed upon selection of the selectable "OK" indicator 812 of FIG. 8 is provided. User interface 900 includes an "exact name matches" display portion 910. As shown in display portion 910, the user is informed that upon initiation of this portion of the series of matching functionalities which comprise the order catalog implementation, the user will be directed to review the order catalog names that matched exactly between the previous healthcare information system and the healthcare information system being configured, implemented and/or maintained and verify that the automatic matching was accurately performed. If the user desires to proceed with the order catalog implementation, the selectable "begin" indicator 912 may be selected.

Turning now to FIG. 10, a screen display of an exemplary user interface 1000 that may be displayed upon selection of the "begin" selectable indicator 912 of the "exact name matches" display portion 910 of FIG. 9 is provided. User interface 1000 is configured to display information informing the user of those order catalog items for which there was an exact match between the existing healthcare information system and the healthcare information system being configured, implemented and/or maintained and to inform the user that to exclude a match, the user may deselect the corresponding match checkbox for that orderable item. Once the user has completed this portion of the reconciliation process, the user may select the selectable "OK" indicator 1010 to move on to the next step.

Figure 11:
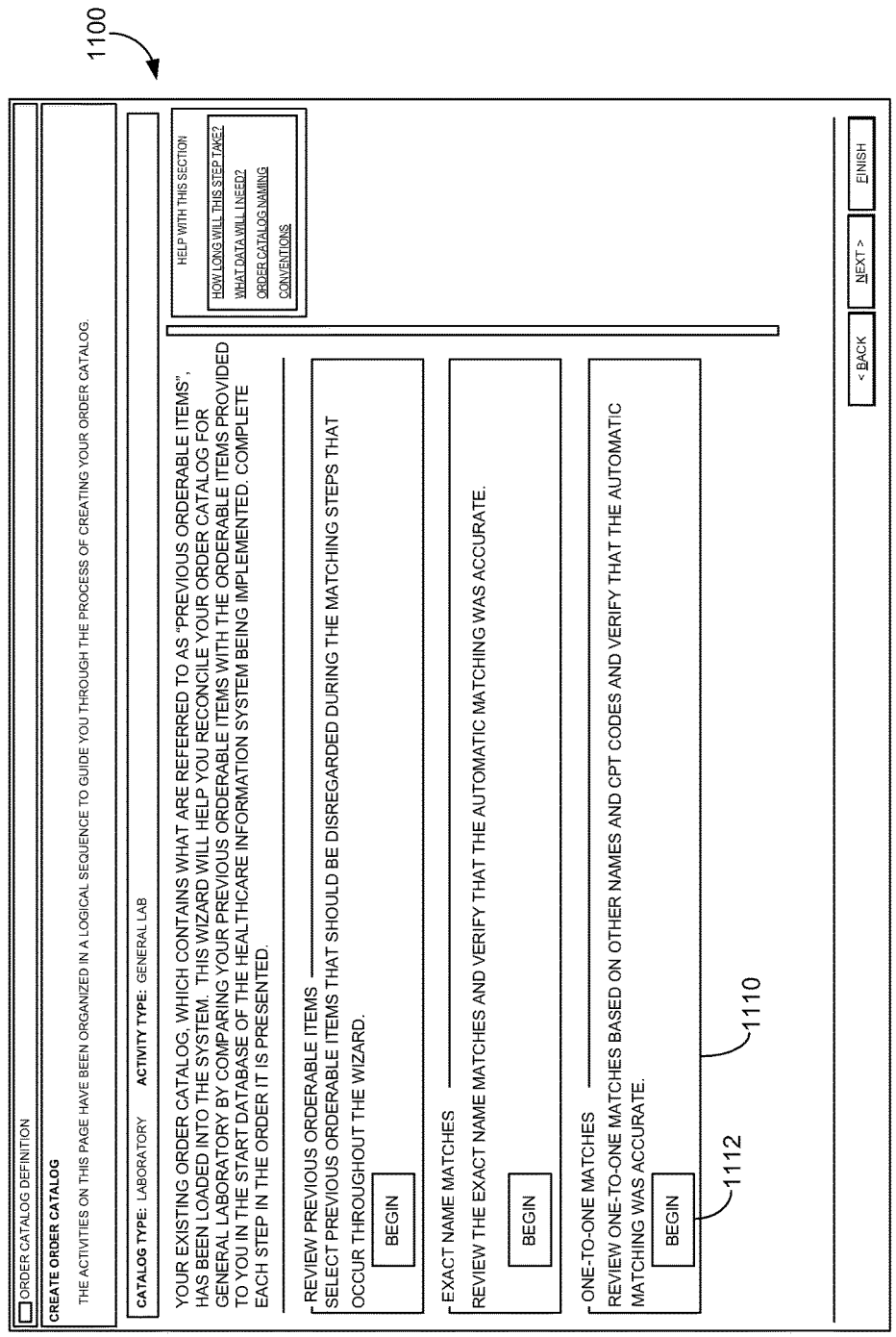
FIG. 11 is a screen display, in accordance with an embodiment of the present invention, of an exemplary user interface that may be displayed upon selection of the "OK" indicator of FIG. 10 illustrating that the next step in the series of order matching functionalities is a "one-to-one" matching functionality.

With reference to FIG. 11, a screen display of an exemplary user interface 1100 that may be displayed upon selection of the selectable "OK" indicator 1010 of FIG. 10 is provided. User interface 1100 includes a "one-to-one matches" display portion 1110. As shown in display portion 1110, the user is informed that upon initiation of this portion of the series of matching functionalities which comprise the order catalog configuration, implementation and/or maintenance, the user will be directed to review the order catalog names that matched one-to-one between the previous healthcare information system and the healthcare information system being configured, implemented and/or maintained based on other names and CPT codes and verify that the automatic matching was accurate. If the user desires to proceed with the order catalog implementation, the selectable "begin" indicator 1112 may be selected.

Turning now to FIG. 12, a screen display of an exemplary user interface 1200 that may be displayed upon selection of the "begin" selectable indicator 1112 of the "one-to-one matches" display portion 1110 of FIG. 11 is provided. User interface 1200 is configured to display information instructing the user to review those order catalog items for which there was a one-to-one match between the existing healthcare information system and the healthcare information system being configured, implemented and/or maintained and to display information informing the user that if the user desires to exclude a match, the user should deselect the corresponding match checkbox for that orderable item. If the user desires to view the actual mapping of the item, the user may select the item from the one-to-one matches item listing. For instance, if a user selects the "acetaminophen" listing 1210 from the one-to-one matches item listing, the screen display 1300 of FIG. 13 may be displayed showing the actual mapping of "acetaminophen" to "acetaminophen level". Once the user has reviewed the information presented in the screen display 1300 of FIG. 13, the user may select the "OK" selectable indicator 1310 to return to the screen display 1200 of FIG. 12.

It should be noted that in the one-to-one matching step of the order catalog portion of the healthcare information system configuration/implementation/maintenance, matching may be performed on the basis of alternate names that have been derived from any number of sources including, but not limited, institutional knowledge supporting the healthcare information system being configured, implemented and/or maintained. For instance, if the institution supporting the healthcare information system has knowledge that many users may refer to "albumin serum" by the alternate name "albumin level", such matching may still be selected as a one-to-one match. Such knowledge may be input, for instance, from the survey-learned data component 228 and input into the survey component 210 of FIG. 2. As such, a user may desire to more closely watch those one-to-one matches that are matched on the basis of alternate names.

Once the user has completed this portion of the reconciliation process, the user may select the selectable "OK" indicator 1212 to move on to the next step.

Figure 14:
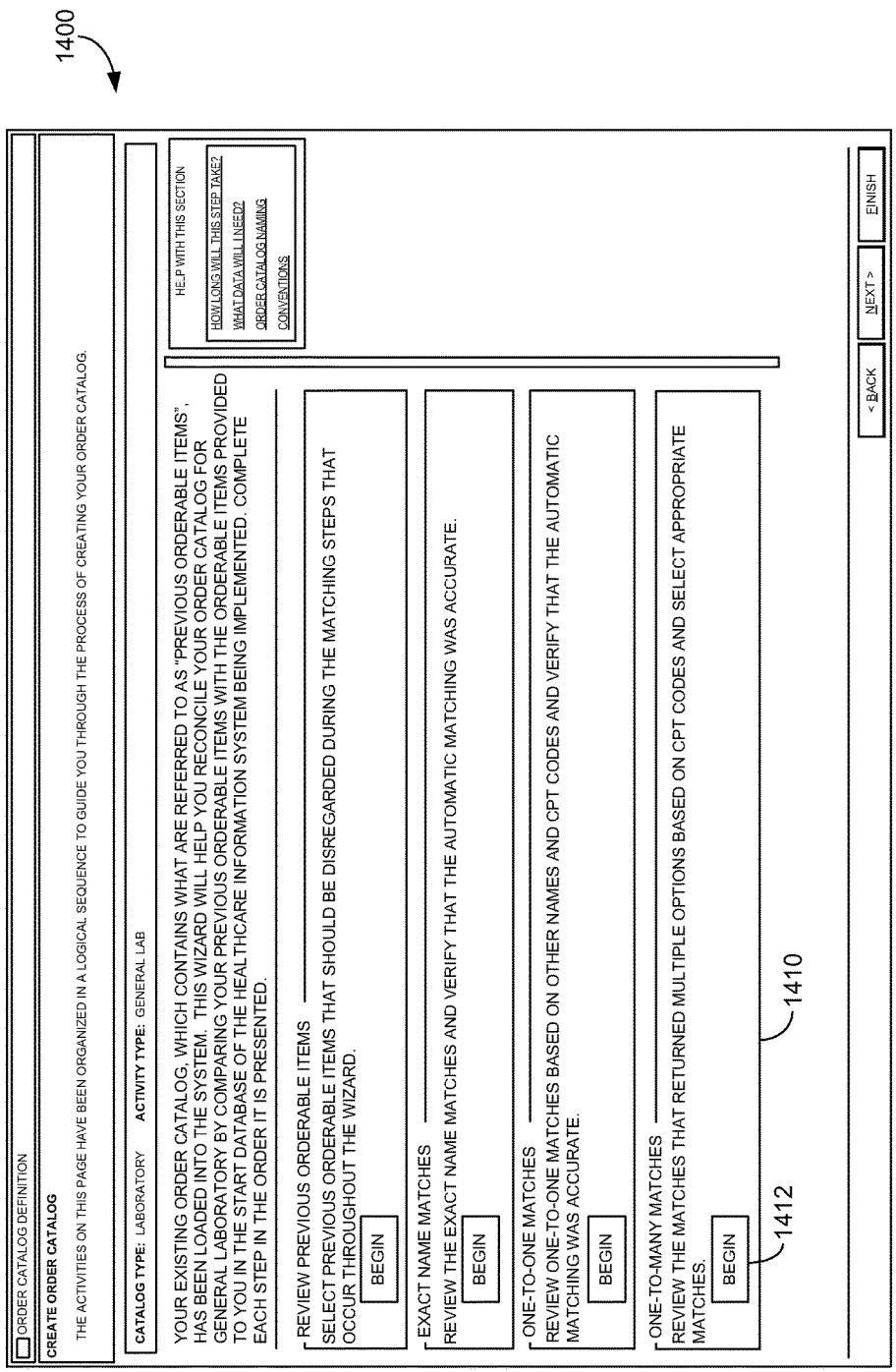
FIG. 14 is a screen display, in accordance with an embodiment of the present invention, of an exemplary user interface that may be displayed upon selection of the "OK" indicator of FIG. 12, illustrating that the next step in the series of order matching functionalities is "one-to-many" matching functionality.

With reference to FIG. 14, a screen display of an exemplary user interface 1400 that may be displayed upon selection of the selectable "OK" indicator 1212 of FIG. 12 is provided. User interface 1400 includes a "one-to-many matches" display portion 1410. As shown in display portion 1410, the user is informed that upon initiation of this portion of the series of matching functionalities which comprise the order catalog configuration, implementation and/or maintenance, the user will be directed to review the order catalog names that returned multiple options between the previous healthcare information system and the healthcare information system being configured, implemented and/or maintained based on CPT codes and select appropriate matches. If the user desires to proceed with the order catalog implementation, the selectable "begin" indicator 1412 may be selected.

Figure 15:
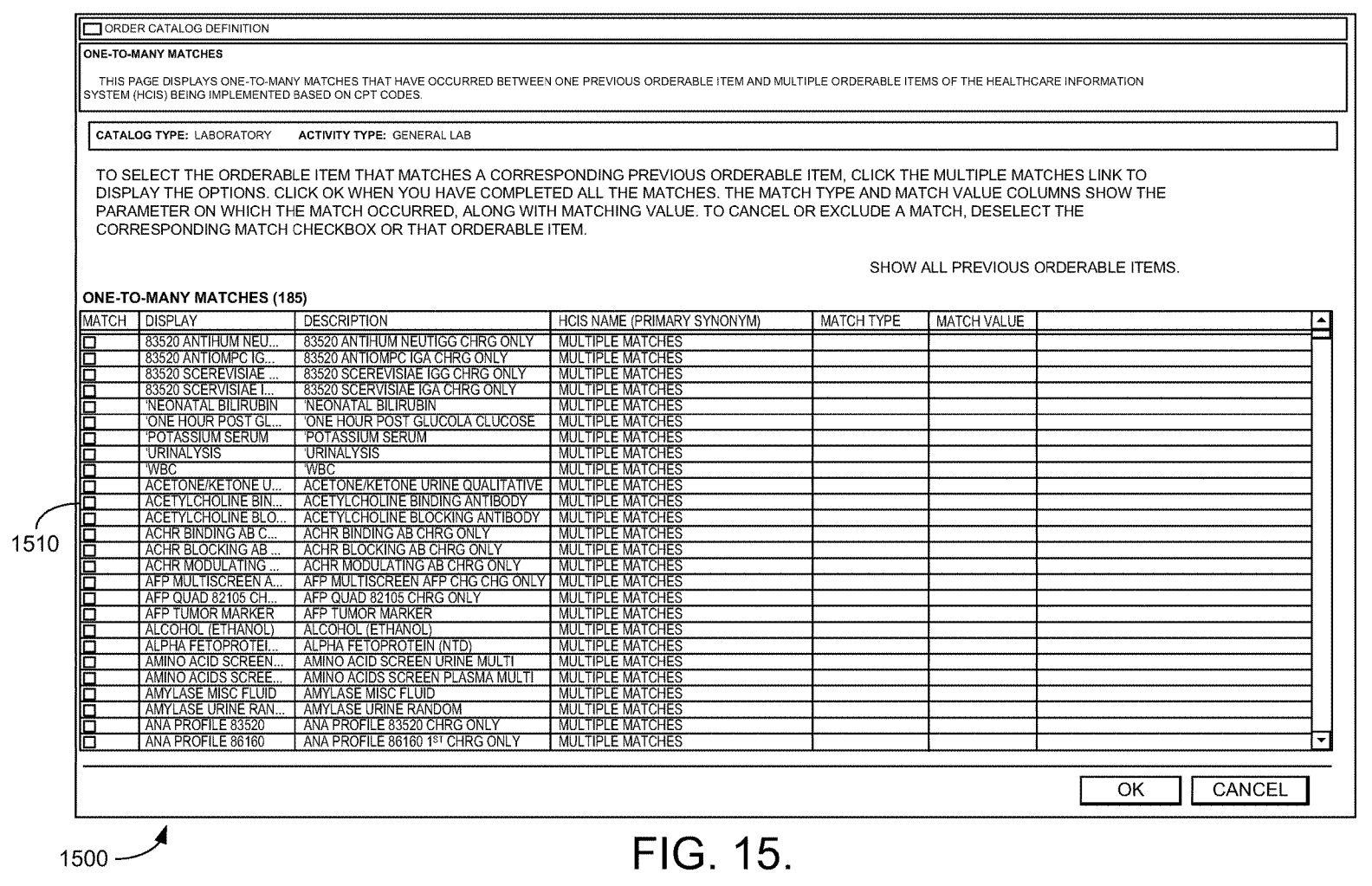
Figure 16:
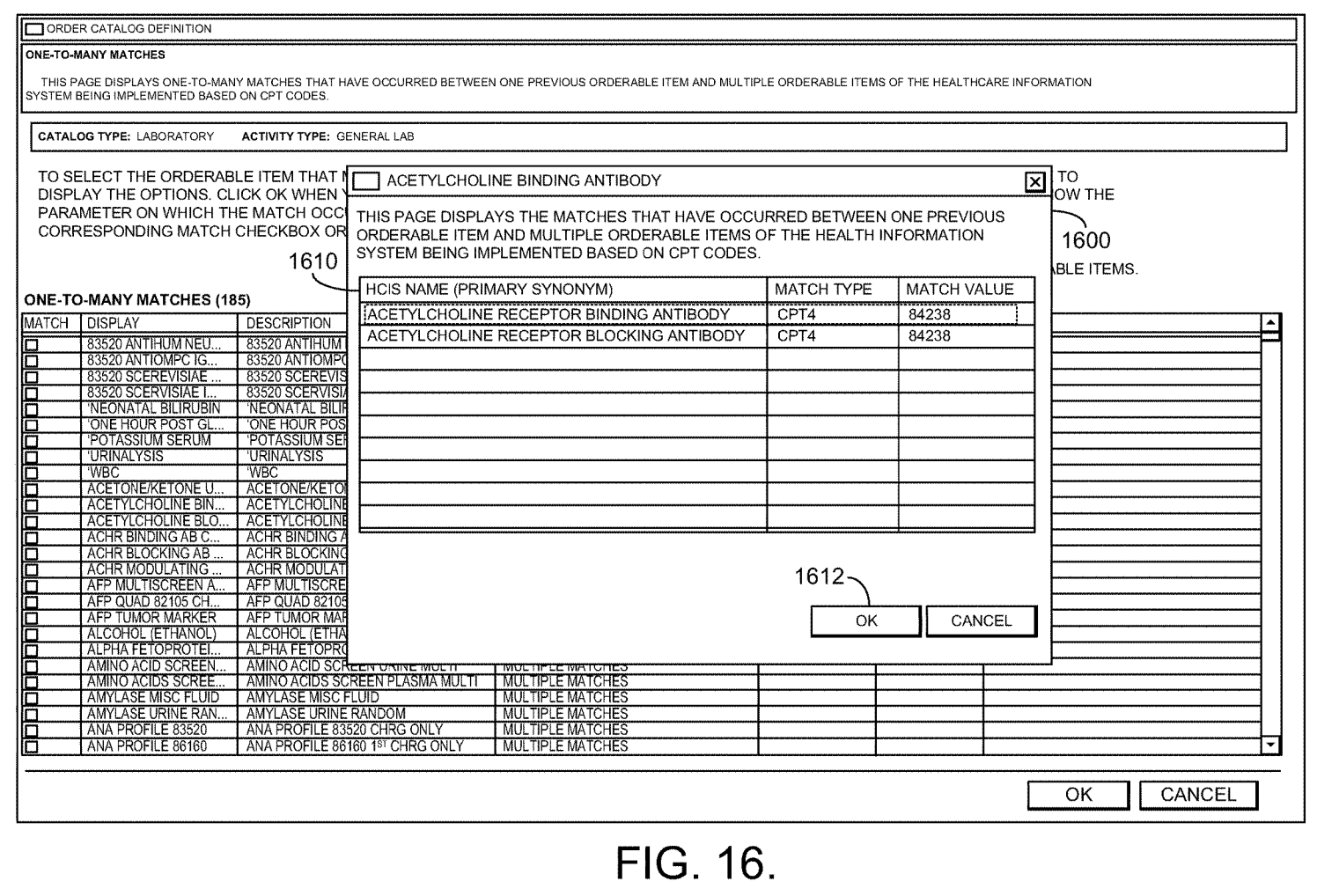

Turning now to FIG. 15, a screen display of an exemplary user interface 1500 that may be displayed upon selection of the "begin" selectable indicator 1412 of the "one-to-many matches" display portion 1410 of FIG. 14 is provided. User interface 1500 includes an informational portion 1510 configured to display information informing the user to select the orderable items of the healthcare information system being configured, implemented and/or maintained that match corresponding orderable items from the existing healthcare information system, the user may click the "multiple matches" link displayed in association with the item to display the options. For instance, suppose a user desires to review and reconcile the multiple matches associated with the "acetylcholine binding antibody" indicator in the one-to-many matches listing of FIG. 15. Upon selection of the "multiple matches" link associated therewith, the screen display 1600 of FIG. 16 may be displayed. Screen display 1600 includes an informational portion 1610 configured to display each of the orderable item names associated with the healthcare information system being implemented that matched to the "acetylcholine binding antibody" orderable item name input from the existing healthcare information system. In the illustrated embodiment, the "acetylcholine binding antibody" orderable item matched to both "acetylcholine receptor binding antibody" and "acetylcholine receptor blocking antibody". At this point, the user may select which of the two matched orderable item names to which the user intends to have the "acetylcholine binding antibody" orderable item name match. In the illustrated embodiment, suppose the user selects the "acetylcholine receptor binding antibody" orderable item name. Subsequently, the user may select the selectable "OK" indicator 1612. Upon such selection, screen display 1700 of FIG. 17 may be displayed.

Note that screen display 1700 is similar to screen display 1500 of FIG. 15 with the exception of the information listed in association with the "acetylcholine binding antibody" order item. The "acetylcholine binding antibody" order item now indicates that a match has been made thereto with the "acetylcholine receptor binding antibody" order catalog item name for the healthcare information system being configured, implemented and/or maintained. Next suppose that the user selects the "acetylcholine blocking antibody" orderable item from the one-to-many matches name listing of FIG. 17. Upon such selection, the screen display 1800 of FIG. 18 may be displayed. While it is known from the previous screen display 1600 of FIG. 16 that the same CPT4 code matched both the "acetylcholine receptor binding antibody" and "acetylcholine receptor blocking antibody" order catalog items for the healthcare information system being configured, implemented and/or maintained, only the "acetylcholine receptor blocking antibody" order catalog item is shown as a possibility for the user to select for reconciliation. This is because the "acetylcholine receptor binding antibody" order catalog item was previously matched to the "acetylcholine binding antibody" and, accordingly, is no longer available to the user for selection. Thus, the options presented to the user are constantly being tailored or flexed based upon information received by the system such that the user is asked only for that information which the system needs to complete configuration, implementation and/or maintenance at any given point in time.

Upon selection of the "OK" selectable indicator 1812 of FIG. 18, the screen display 1900 of FIG. 19 may be presented which now illustrates that both the "acetylcholine binding antibody" and "acetylcholine blocking antibody" order catalog item names from the existing healthcare information system have been reconciled with order catalog item names from the healthcare information system being configured, implemented and/or maintained. Once the user has completed this portion of the reconciliation process, the user may select the selectable "OK" indicator 1910 to proceed to the next step.

Figure 20:
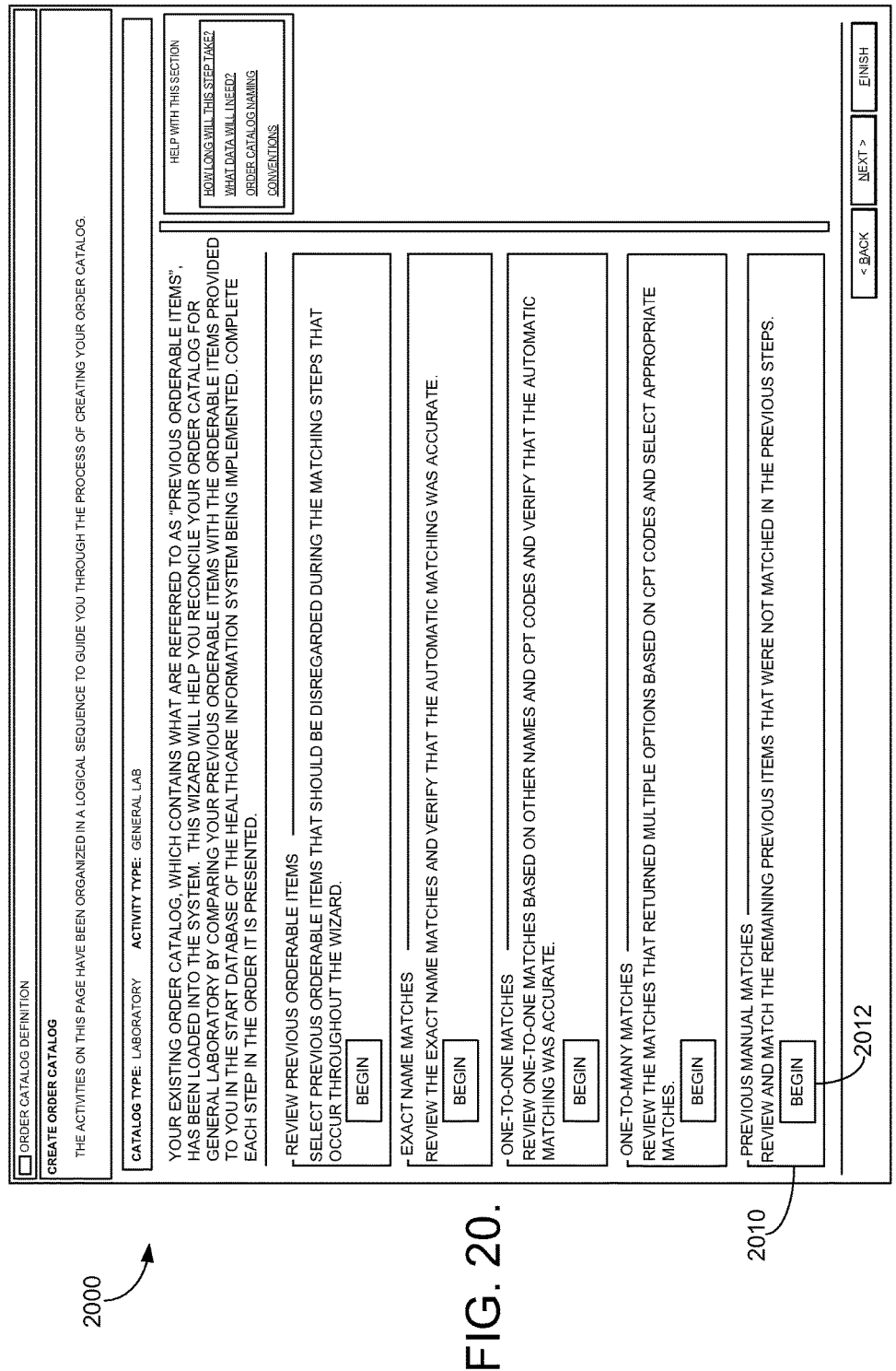
FIG. 20 is a screen display that may be displayed upon selection of the "OK" selectable indicator of FIG. 19 illustrating that the next step in the series of order matching functionalities is a "manual" matching functionality, in accordance with an embodiment of the present invention.

With reference to FIG. 20, a screen display of an exemplary user interface 2000 that may be displayed upon selection of the selectable "OK" indicator 1910 of FIG. 19 is provided. User interface 2000 includes a "previous manual matches" display portion 2010. As shown in display portion 2010, the user is informed that upon initiation of this portion of the series of matching functionalities which comprise the order catalog configuration, implementation and/or maintenance, the user will be directed to review the order catalog names from the previous healthcare information system that were not matched to order catalog names in the healthcare information system being configured, implemented and/or maintained in the previous steps and match them, if possible. If the user desires to proceed with the order catalog implementation, the selectable "begin" indicator 2012 may be selected.

Turning now to FIG. 21, a screen display of an exemplary user interface 2100 that may be displayed upon user selection of the "begin" selectable indicator 2010 of the "previous manual matches" display portion 2010 of FIG. 20 is provided. User interface 2100 is configured to display information informing the user that unmatched orderable items from the existing healthcare information system may be manually matched to unmatched orderable items for the healthcare information system being configured, implemented and/or maintained. Once the user has completed this portion of the reconciliation process, the user may select the selectable "OK" indicator 2110 to move on to the next step.

Figure 22:
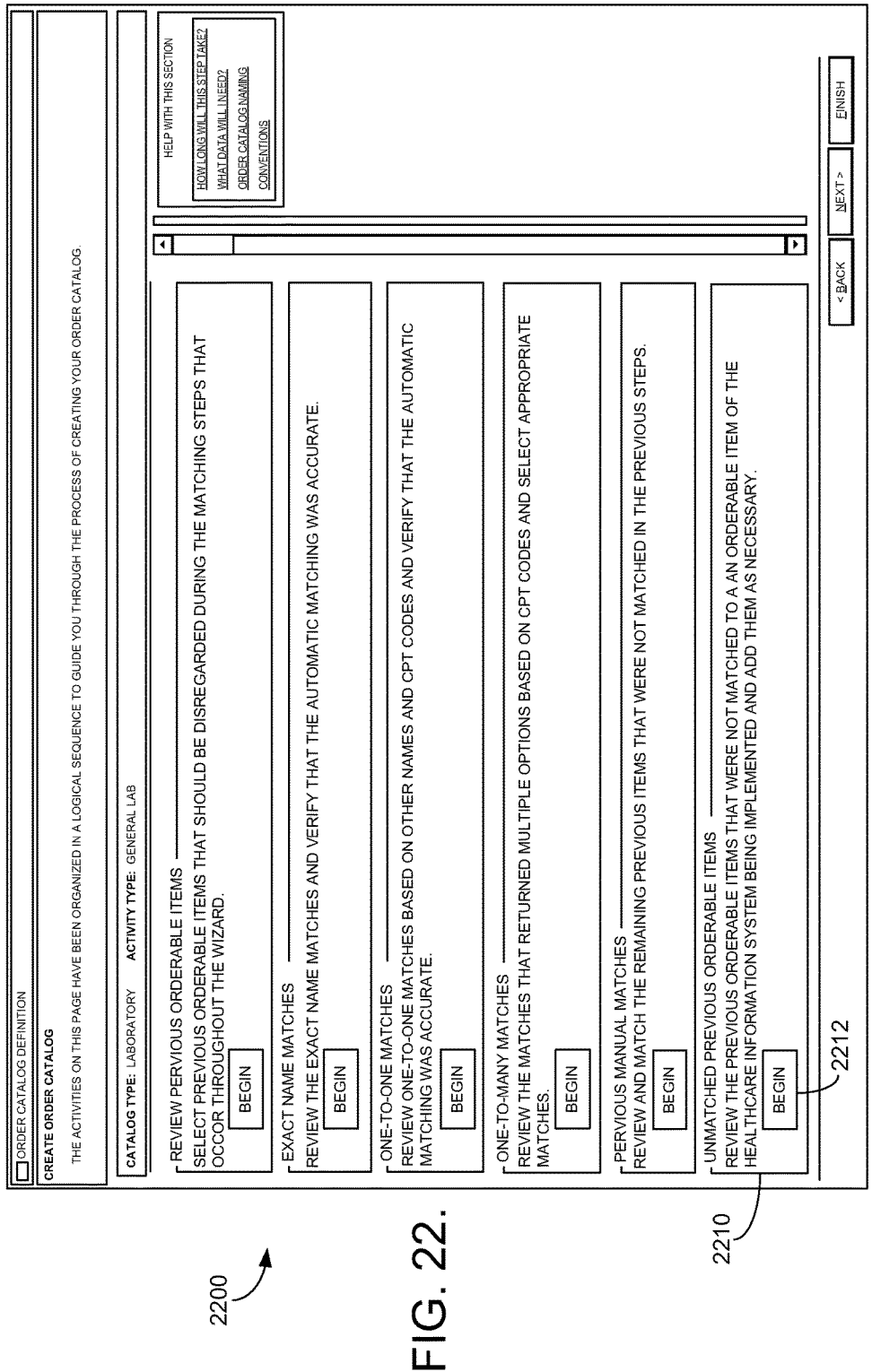
FIG. 22 is a screen display, in accordance with an embodiment of the present invention, that may be displayed upon selection of the "OK" selectable indicator of FIG. 21, illustrating that the next step in the series of order matching functionalities is review of unmatched previous orderable items.

With reference to FIG. 22, a screen display of an exemplary user interface 2200 that may be displayed upon selection of the selectable "OK" indicator 2110 of FIG. 21 is provided. User interface 2200 includes an "unmatched previous orderable items" display portion 2210. As shown in display portion 2210, the user is informed that upon initiation of this portion of the series of matching functionalities which comprise the order catalog configuration, implementation and/or maintenance, the user will be directed to review the order catalog items from the existing healthcare information system that were not matched to an order catalog item in the healthcare information system being configured, implemented and/or maintained and add them, as necessary. If the user desires to proceed with the order catalog configuration, implementation and/or maintenance, the selectable "begin" indicator 2212 may be selected.

Turning now to FIG. 23, a screen display of an exemplary user interface 2300 that may be displayed upon user selection of the "begin" selectable indicator 2212 of the "unmatched previous orderable items" display portion 2210 of FIG. 22 is provided. User interface 2300 is configured to display information informing the user to review the unmatched orderable items from the existing healthcare information system and select those which the user desires to add to the order catalog. Once the user has completed this portion of the reconciliation process, the user may select the selectable "OK" indicator 2310 to move on to the next step.

Figure 24:
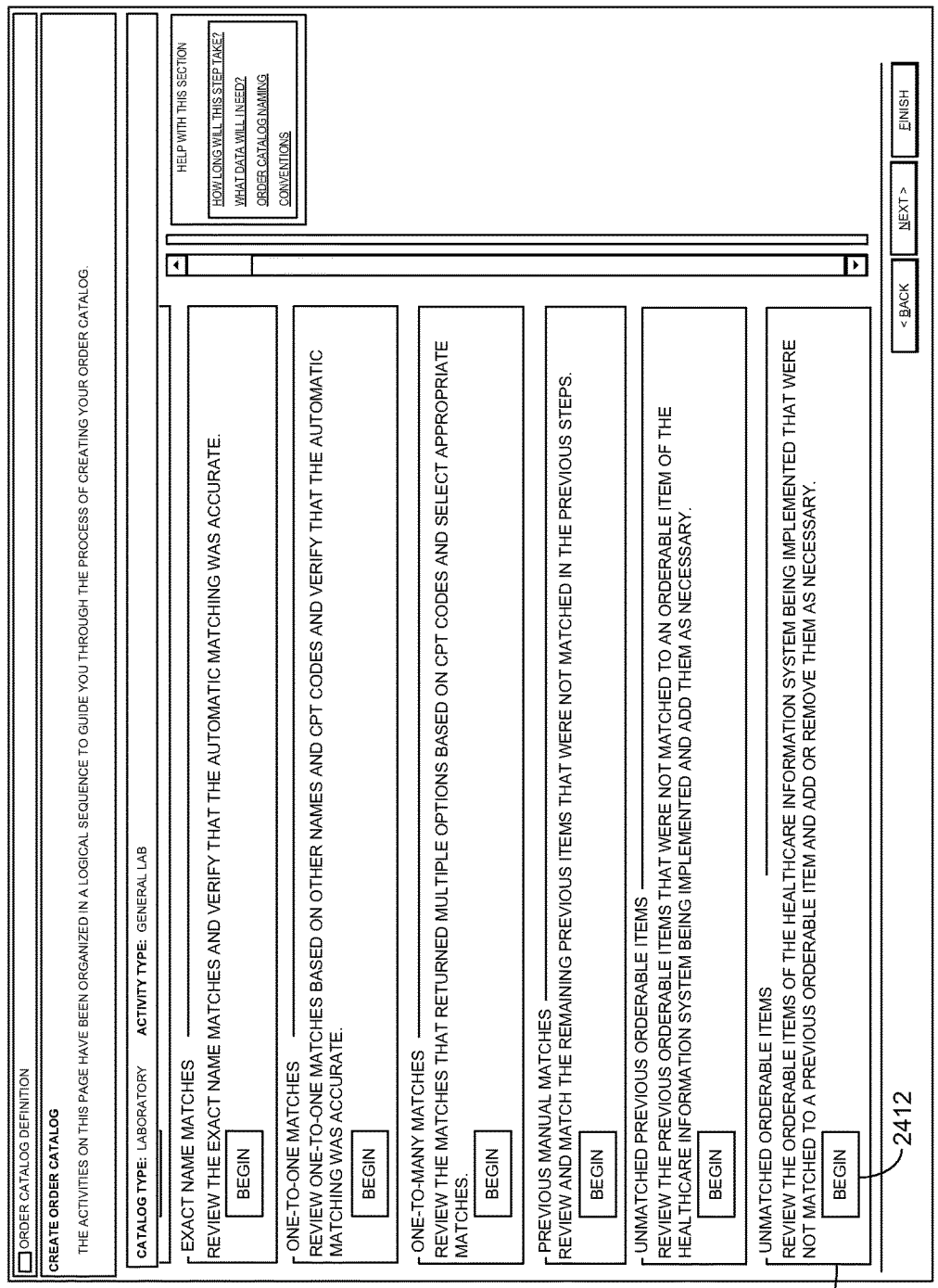
FIG. 24 is a screen display, in accordance with an embodiment of the present invention, that may be displayed upon selection of the "OK" selectable indicator of FIG. 23 illustrating that the next step in the series of order matching functionalities is review of unmatched orderable items of the healthcare information system being implemented.

With reference to FIG. 24, a screen display of an exemplary user interface 2400 that may be displayed upon selection of the selectable "OK" indicator 2310 of FIG. 23 is provided. User interface 2400 includes an "unmatched orderable items" display portion 2410. As shown in display portion 2410, the user is informed that upon initiation of this portion of the series of matching functionalities which comprise the order catalog implementation, the user will be directed to review the order catalog items of the healthcare information system being configured, implemented and/or maintained that were not matched to an order catalog item in the existing healthcare information system and add or remove them, as necessary. If the user desires to proceed with the order catalog configuration, implementation and/or maintenance, the selectable "begin" indicator 2412 may be selected.

Turning now to FIG. 25, a screen display of an exemplary user interface 2500 that may be displayed upon user selection of the "begin" selectable indicator 2412 of the "unmatched orderable items" display portion 2410 of FIG. 24 is provided. User interface 2500 is configured to display information instructing the user to review those order catalog items from the healthcare information system being configured, implemented and/or maintained which were not matched to any orderable items from the existing healthcare information system and select or deselect based upon their preferences with regard to including them in the order catalog. Once the user has completed this portion of the reconciliation process, the user may select the selectable "OK" indicator 2510 to move on to the next step.

Figure 26:
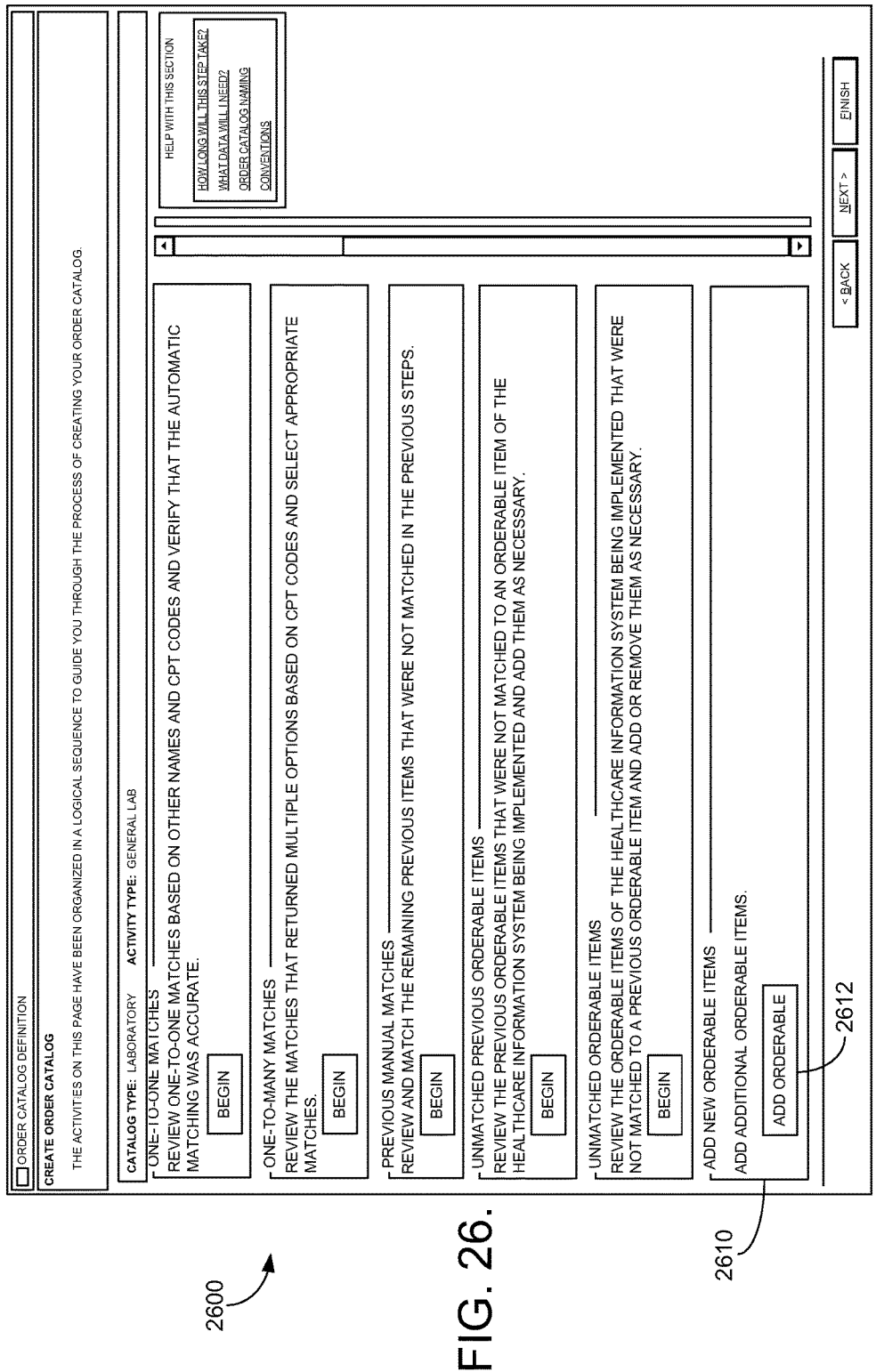
FIG. 26 is a screen display, in accordance with an embodiment of the present invention, that may be displayed upon selection of the "OK" selectable indicator of FIG. 25 illustrating that the next step in the series of order matching functionalities is providing the user with the opportunity to add new orderable items, if desired.

With reference to FIG. 26, a screen display of an exemplary user interface 2600 that may be displayed upon selection of the selectable "OK" indicator 2510 of FIG. 25 is provided. User interface 2600 includes an "add new orderable items" display portion 2610. As shown in display portion 2610, the user is informed that upon initiation of this portion of the series of matching functionalities which comprise the order catalog configuration, implementation and/or maintenance, the user will be directed to add any desired new orderable items. If the user desires to proceed with the order catalog configuration, implementation and/or maintenance, the selectable "add orderable" indicator 2612 may be selected.

Turning now to FIG. 27, a screen display of an exemplary user interface 2700 that may be displayed upon user selection of the "add orderable" selectable indicator 2612 of the "add new orderable items" display portion 2610 of FIG. 26 is provided. User interface 2700 is configured to display interactive fields into which a user may manually enter those order catalog items they may want to add to their order catalog. Once the user has completed this portion of the reconciliation process, the user may select the selectable "OK" indicator 2710 to proceed to the next step. At this point, the user will be returned to the screen display 2600 of FIG. 26 and directed to select the selectable "finish" indicator as the general laboratory order catalog wizard will have been completed.

As can be understood, the present invention provides computerized systems and methods for the automated configuration, implementation and/or maintenance of a healthcare information system. Such configuration or implementation may include building of a healthcare information system from the ground level or modifying or converting an existing healthcare information system.

The present invention has been described in relation to particular embodiments, which are intended in all respects to be illustrative rather than restrictive. Alternative embodiments will become apparent to those of ordinary skill in the art to which the present invention pertains without departing from its scope.

From the foregoing, it will be seen that this invention is one well adapted to attain all the ends and objects set forth above, together with other advantages which are obvious and inherent to the system and method. It will be understood that certain features and subcombinations are of utility and may be employed without reference to other features and subcombinations. This is contemplated and within the scope of the claims.

What is claimed is:

1. One or more computer storage devices having computer-executable instructions embodied thereon that, when executed, performing a method of displaying in a clinical environment for building a customized healthcare information system based on an existing healthcare information system by selectively associating, through directed user input, content items from the existing healthcare information system with pre-configured alternatives, the pre-configured alternatives configured for use in the customized healthcare information system and configured to be options to represent one or more content items from the existing healthcare information system, the method comprising:

receiving, from an interactive display a survey component, a first content item from an existing healthcare information system for building a customized healthcare information system, wherein the first content item comprises a first clinical laboratory orderable items;

determining, via the survey component, that the first content item is an exact name match with a pre-configured content item for use in the customized healthcare information system;

presenting, via the interactive display the survey component, a representation of the exact name match between the first content item and the pre-configured content item for verification, from a user, of the exact name match, the user being a healthcare facility or at least one of a healthcare facility personnel, wherein the survey component is configured to present a plurality of screen displays from which the user may input information to build the customized healthcare information system;

receiving via the interactive display verification from the user of the exact name match between the first content item and the pre-configured content item for use in the customized healthcare information system;

receiving via the interactive display, at a survey component, a second content item from an existing healthcare information system for building a customized healthcare information system, wherein the second content item comprises a second clinical laboratory orderable item;

determining, via the survey component, a plurality of pre-configured alternatives for user selection to reconcile the second content item from the existing healthcare information system with one or more pre-configured alternatives of the plurality of pre-configured alternatives, the plurality of pre-configured alternatives configured for use in the customized healthcare information system and configured to be options to represent the second content item in the customized healthcare information system, wherein each of the plurality of pre-configured alternatives are determined utilizing pre-configured content that comprises survey-specific tables that contain options for configuring, implementing, or maintaining the customized healthcare information system, facility and personnel-specific content derived from the existing healthcare information system, and facility and personnel profiles, wherein the derived facility and personnel-specific content is extracted utilizing data mining techniques performed on HL-7 transactions within the existing healthcare information system, and wherein the survey-specific tables are extracted utilizing data mining techniques performed on the existing healthcare information system;

presenting, via the survey component on the interactive display, the plurality of pre-configured alternatives for user selection;

directing the user via interactive display through the process of selecting one pre-configured alternative of the plurality of pre-configured alternatives to reconcile the second content item from the existing healthcare information system with the one pre-configured alternative of the plurality of pre-configured alternatives for use in the customized healthcare information system;

receiving via the interactive display, at the survey component, user selection of the one pre-configured alternative of the plurality of pre-configured alternatives for association with the second content item in order to reconcile the second content item from the existing healthcare information system with the one pre-configured alternative of the plurality of pre-configured alternatives.

2. The one or more computer storage devices of claim 1, wherein at least one of the plurality of pre-configured alternatives is based upon a CPT code associated with the second clinical orderable item.

3. The one or more computer storage devices of claim 1, wherein the method further comprises, prior to the presenting, via the survey component, the plurality of pre-configured alternatives for user selection, displaying information regarding order catalog naming conventions that are associated with the customized healthcare information system.

4. The one or more computer storage devices of claim 1, further comprising receiving via the interactive display user input to add unmatched clinical laboratory orderable items.

5. The one or more computer storage devices of claim 1, further comprising displaying on an interactive display the first plurality of pre-configured alternatives and second plurality of pre-configured alternatives in a sequential ordered list.

6. A method in a clinical environment for building a customized healthcare information system based on an existing healthcare information system by selectively associating content items from the existing healthcare information system with pre-configured alternatives, based upon directed user input, the pre-configured alternatives configured for use in the customized healthcare information system and configured to be options to represent one or more content items from the existing healthcare information system, the method being performed by one or more computing devices including at least one processor and one or more computer-readable media, the method comprising:

receiving from an interactive display at a survey component a plurality of content items from an existing healthcare information system for building a customized healthcare information system, wherein each of the plurality of content items is a clinical laboratory orderable item;

determining via the survey component that a first content item of the plurality of content items is an exact name match with a pre-configured content item for use in the customized healthcare information system;

presenting via the interactive display the survey component a representation of the exact name match between the first content item and the pre-configured content item for verification, from a user, of the exact name match, the user being a healthcare facility or at least one of a healthcare facility personnel, wherein the survey component is configured to present a plurality of screen displays from which the user may input information to build the customized healthcare information system;

receiving via the interactive display verification from the user of the exact name match between the first content item and the pre-configured content item for use in the customized healthcare information system;

determining, via the survey component, a first plurality of pre-configured alternatives for user selection to reconcile a second content item of the plurality of content items from the existing healthcare information system with one or more pre-configured alternatives, wherein the first plurality of pre-configured alternatives are configured for use in the customized healthcare information system and configured to be options to represent the second content item of the plurality of content items in the customized healthcare information system, wherein each of the first plurality of pre-configured alternatives are determined utilizing pre-configured content that comprises survey-specific tables that contain options for configuring, implementing, or maintaining the customized healthcare information system, facility and personnel-specific content derived from the existing healthcare information system, and a facility and personnel profile, wherein the derived facility and personnel-specific content is extracted utilizing data mining techniques performed on HL-7 transactions within the existing healthcare information system, and wherein the survey-specific tables are extracted utilizing data mining techniques performed on the existing healthcare information system;

presenting via the survey component on the interactive display, at least the second of the plurality of content items for association with the first plurality of pre-configured alternatives;

directing the user via interactive display through the process of selecting at least one pre-configured alternative of the first plurality of pre-configured alternatives to reconcile the second content item from the existing healthcare information system with the at least one pre-configured alternative of the first plurality of pre-configured alternatives for use in the customized healthcare information system;

receiving via the interactive display, at the survey component, user selection of the at least one pre-configured alternative of the first plurality of pre-configured alternatives for association with the second of the plurality of content items;

determining, via the survey component, a second plurality of pre-configured alternatives for user selection to reconcile a third content item of the plurality of content items from the existing healthcare information system with one or more pre-configured alternatives of the second plurality of pre-configured alternatives, wherein the second plurality of pre-configured alternatives are configured for use in the customized healthcare information system and configured to be options to represent the third content item of the plurality of content items in the customized healthcare information system; and presenting via the survey component at least the third of the plurality of content items for association with the second plurality of pre-configured alternatives, wherein the at least one pre-configured alternative of the first plurality of pre-configured alternatives selected for association with the second content item is not presented with the second plurality of pre-configured alternatives.

7. The method of claim 6, wherein at least one of the first plurality of preconfigured alternatives is based upon a CPT code associated with the clinical laboratory orderable item.

8. The method of claim 6, further comprising utilizing information extracted from the user selection of the at least one pre-configured alternative of the first plurality of pre-configured alternatives for association with the second of the plurality of content items to direct the user through the process of selecting a pre-configured alternative of the second plurality of pre-configured alternatives for association with the third of the plurality of content items.

9. The method of claim 6, further comprising, prior to the presenting via the survey component at least the second of the plurality of content items for association with the first plurality of pre-configured alternatives, displaying information regarding order catalog naming conventions that are associated with the customized healthcare information system.

* * * * *